(12) United States Patent
Skidmore et al.

(10) Patent No.: US 7,227,140 B2
(45) Date of Patent: Jun. 5, 2007

(54) METHOD, SYSTEM AND DEVICE FOR MICROSCOPIC EXAMINATION EMPLOYING FIB-PREPARED SAMPLE GRASPING ELEMENT

(75) Inventors: George Skidmore, Richardson, TX (US); Matthew D. Ellis, Allen, TX (US); Aaron Geisberger, Dallas, TX (US); Kenneth Bray, Garland, TX (US); Kimberly Tuck, Dallas, TX (US); Robert Folaron, Plano, TX (US)

(73) Assignee: Zyvex Instruments, LLC, Richardson, TX (US)

( * ) Notice: Subject to any disclaimer, the term of this patent is extended or adjusted under 35 U.S.C. 154(b) by 0 days.

(21) Appl. No.: 10/948,385

(22) Filed: Sep. 23, 2004

(65) Prior Publication Data

US 2005/0178980 A1 Aug. 18, 2005

Related U.S. Application Data

(60) Provisional application No. 60/546,840, filed on Feb. 23, 2004, provisional application No. 60/505,026, filed on Sep. 23, 2003.

(51) Int. Cl.
*G21G 5/00* (2006.01)
(52) U.S. Cl. .............. 250/307; 250/492.21; 250/492.3; 250/442.11; 702/84; 438/17
(58) Field of Classification Search ................ None
See application file for complete search history.

(56) References Cited

U.S. PATENT DOCUMENTS 2,782,682 A 2/1957 Browning et al.
3,134,942 A 5/1964 Rhodes
3,535,515 A 10/1970 Jones et al.
3,714,423 A 1/1973 Lucas
4,019,073 A 4/1977 Vishnevsky et al.
4,463,257 A 7/1984 Simpkins et al.
4,587,431 A 5/1986 Uemura
4,601,551 A 7/1986 Pettingell et al.
4,610,475 A 9/1986 Heiserman
4,672,256 A 6/1987 Okuno et al.

(Continued)

FOREIGN PATENT DOCUMENTS

CN 2158072 Y 1/1994

(Continued)

OTHER PUBLICATIONS

Erickson, "Gate Fault Isolation and Parametric Characterization through the use of Atomic Force Probing", Multiprobe, Inc. Santa Barbara, California.

(Continued)

*Primary Examiner*—Jack Berman
*Assistant Examiner*—Zia R. Hashmi
(74) *Attorney, Agent, or Firm*—Haynes and Boone, LLP

(57) ABSTRACT

A method including, in one embodiment, severing a sample at least partially from a substrate by cutting the substrate with a focused ion beam (FIB), capturing the substrate sample by activating a grasping element, and separating the captured sample from the substrate. The captured sample may be separated from the substrate and transported to an electron microscope for examination.

69 Claims, 9 Drawing Sheets

U.S. PATENT DOCUMENTS

| | | | |
|---|---|---|---|
| 4,678,955 A | 7/1987 | Toda | |
| 4,729,646 A | 3/1988 | Clark et al. | |
| 4,736,129 A | 4/1988 | Endo et al. | |
| 4,798,989 A | 1/1989 | Miyazaki et al. | |
| 4,850,779 A | 7/1989 | Cashell et al. | |
| 4,874,979 A | 10/1989 | Rapp | |
| 4,919,001 A | 4/1990 | Ogiwara et al. | |
| 5,036,205 A | 7/1991 | Clement et al. | |
| 5,055,680 A | 10/1991 | Kesmodel et al. | |
| 5,068,535 A | 11/1991 | Rabalais | |
| 5,081,353 A | 1/1992 | Yamada et al. | |
| 5,089,740 A | 2/1992 | Ono | |
| 5,117,110 A | 5/1992 | Yasutake | |
| 5,124,645 A | 6/1992 | Rhoden et al. | |
| 5,225,683 A | 7/1993 | Suzuki et al. | |
| 5,237,238 A | 8/1993 | Berghaus et al. | |
| 5,270,552 A | 12/1993 | Ohnishi et al. | |
| 5,332,275 A | 7/1994 | Conway et al. | |
| 5,338,997 A | 8/1994 | Benecke | |
| 5,412,503 A | 5/1995 | Nederlof | |
| 5,455,420 A | 10/1995 | Ho et al. | |
| 5,458,387 A | 10/1995 | Conway et al. | |
| 5,493,236 A | 2/1996 | Ishii et al. | |
| 5,510,615 A | 4/1996 | Ho et al. | |
| 5,538,305 A | 7/1996 | Conway et al. | |
| 5,568,004 A | 10/1996 | Kleindiek | |
| 5,589,723 A | 12/1996 | Yoshida et al. | |
| 5,635,836 A | 6/1997 | Kirtley et al. | |
| 5,677,709 A | 10/1997 | Miura et al. | |
| 5,727,915 A | 3/1998 | Suzuki | |
| 5,756,997 A | 5/1998 | Kley | |
| 5,886,684 A | 3/1999 | Miura et al. | |
| 5,895,084 A | 4/1999 | Mauro | |
| 5,922,179 A | 7/1999 | Mitro et al. | |
| 5,939,816 A | 8/1999 | Culp | |
| 5,973,471 A | 10/1999 | Miura et al. | |
| 5,989,779 A | 11/1999 | Hatakeyama et al. | |
| 5,994,820 A | 11/1999 | Kleindiek | |
| 5,998,097 A | 12/1999 | Hatakeyama et al. | |
| 6,000,280 A | 12/1999 | Miller et al. | |
| 6,002,136 A | 12/1999 | Naeem | |
| 6,007,696 A | 12/1999 | Takayasu et al. | |
| 6,010,831 A | 1/2000 | Hatakeyama et al. | |
| 6,043,548 A | 3/2000 | Cahen et al. | |
| 6,048,671 A | 4/2000 | Hatakeyama et al. | |
| 6,111,336 A | 8/2000 | Yoshida et al. | |
| 6,127,681 A | 10/2000 | Sato et al. | |
| 6,127,682 A | 10/2000 | Nakamoto | |
| 6,188,161 B1 | 2/2001 | Yoshida et al. | |
| 6,198,299 B1 | 3/2001 | Hollman | |
| 6,210,988 B1 | 4/2001 | Howe et al. | |
| 6,268,958 B1 | 7/2001 | Furuhashi | |
| 6,279,007 B1 | 8/2001 | Uppala | |
| 6,279,389 B1 | 8/2001 | Adderton et al. | |
| 6,346,710 B1 | 2/2002 | Ue | |
| 6,403,968 B1 | 6/2002 | Hazaki et al. | |
| 6,420,722 B2 | 7/2002 | Moore et al. | |
| 6,422,077 B1 | 7/2002 | Krauss et al. | |
| 6,448,622 B1 | 9/2002 | Franke et al. | |
| 6,452,307 B1 | 9/2002 | Olin et al. | |
| 6,501,289 B1 | 12/2002 | Takekoshi | |
| 6,538,254 B1 | 3/2003 | Tomimatsu et al. | |
| 6,539,519 B1 | 3/2003 | Meeker | |
| 6,576,900 B2 | 6/2003 | Kelly et al. | |
| 6,580,076 B1 | 6/2003 | Miyazaki | |
| 6,583,413 B1 | 6/2003 | Shinada et al. | |
| 6,597,359 B1 | 7/2003 | Lathrop | |
| 6,603,239 B1 | 8/2003 | Michely et al. | |
| 6,627,889 B2 | 9/2003 | Ochiai et al. | |
| 6,664,552 B2 | 12/2003 | Shichi et al. | |
| 6,690,101 B2 | 2/2004 | Magnussen et al. | |
| 6,777,674 B2 | 8/2004 | Moore et al. | |
| 6,841,788 B1 | 1/2005 | Robinson et al. | |
| 6,865,509 B1 | 3/2005 | Hsiung et al. | |
| 6,891,170 B1 | 5/2005 | Yu et al. | |
| 6,927,400 B2 | 8/2005 | Rasmussen | |
| 6,967,335 B1 | 11/2005 | Dyer et al. | |
| 6,982,429 B2 | 1/2006 | Robinson et al. | |
| 6,986,739 B2 | 1/2006 | Warren et al. | |
| 2001/0044156 A1 | 11/2001 | Kelly et al | |
| 2002/0000522 A1* | 1/2002 | Alani | 250/492.3 |
| 2002/0064341 A1 | 5/2002 | Fauver et al. | |
| 2002/0121614 A1 | 9/2002 | Moore | |
| 2002/0125427 A1 | 9/2002 | Chand et al. | |
| 2002/0138353 A1 | 9/2002 | Schreiber et al. | |
| 2002/0166976 A1 | 11/2002 | Sugaya et al. | |
| 2002/0195422 A1* | 12/2002 | Sievers et al. | 216/62 |
| 2003/0042921 A1 | 3/2003 | Hollman | |
| 2003/0089852 A1 | 5/2003 | Ochiai et al. | |
| 2003/0089860 A1* | 5/2003 | Asjes | 250/442.11 |
| 2003/0137539 A1 | 7/2003 | Dees | |
| 2003/0187867 A1 | 10/2003 | Smartt | |
| 2003/0212725 A1 | 11/2003 | Ovshinsky et al. | |
| 2004/0205093 A1 | 10/2004 | Li et al. | |
| 2004/0245466 A1 | 12/2004 | Robinson et al. | |
| 2005/0029467 A1 | 2/2005 | Yu et al. | |
| 2005/0184028 A1 | 8/2005 | Baur et al. | |
| 2005/0184236 A1 | 8/2005 | Baur et al. | |
| 2006/0192116 A1 | 8/2006 | Baur et al. | |

FOREIGN PATENT DOCUMENTS

| | | |
|---|---|---|
| DE | 19524907 A1 | 1/1997 |
| EP | 0927880 | 7/1999 |
| JP | 2072535 | 3/1990 |
| JP | 5018706 | 1/1993 |
| JP | 11135051 A | 5/1999 |
| JP | 2001198896 A | 7/2001 |
| JP | 2002033366 A | 1/2002 |
| WO | WO96/13724 | 5/1996 |
| WO | WO 96/20495 | 7/1996 |
| WO | WO 00/10191 | 8/1999 |
| WO | WO01/09965 | 2/2001 |
| WO | WO02/16089 | 2/2002 |

OTHER PUBLICATIONS

Dr. Volker Klocke Nanotechnik, Technical Data from Klocke Nanotechnik Websites, Aachen, Germany, 1998, 127 pages and CD ROM with movie.

Yu et al., "Three-Dimensional Manipulation of Carbon Nanotubes Under a Scanning Electron Microscope", Nanotechnology 10 (1999), pp. 244-252.

Fatikow et al., "A Flexible Microbot-Based Microassembly Station", Emerging Technologies and Factory Automation, 1999. Proceeding ETFA '99. 1999 7th IEEE International Conference, Barcelona, Spain Oct. 18-21, 1999, Piscataway, NJ USA, pp. 397-406.

"Investment Approaches: Lux NanoSphere: Measurement", Nanotechnology, The Nanotech Report 2001, pp. 122-136.

"IDS 10000cs", Schlumberger Semiconductor Solutions, San Jose, California, Aug. 2001.

"Electrical Characterization of Transistors in an SRAM Array for the 90nm Process Node", Multi Probe, Inc., Santa Barbara, California, Application Note: MPI 011603, 2002.

International Search Report PCT/US03/16695, dated Sep. 25, 2003.

International Search Report PCT/US03/16750, dated Sep. 25, 2003.

Gupta, "Attaching a Nanotube to a Zyvex S100 Nanomanipulator End Effector", Zyvex Corporation, Richardson, Texas, Document: S1EE-ZZAN-001a, 2004.

Gupta, et al., "Measuring Electrical Breakdown of a Dielectric-Filled Trench Used for Electrical Isolation of Semiconductor Devices", Zyvex Corporation, Richardson, Texas, Document: MEBD-ZZAN-001a, 2004.

Hartman, "Mechanical Measurement of Individual Carbon Nanotubes Using MEMS and the S100 Nanomanipulator", Zyvex Corporation, Richardson, Texas, Document: MMIC-ZZAN-001b, 2004.

Hochberg et al., "Four Point Probe I-V Electrical Measurements Using the Zyvex Test System Employing a Keithley 4200", Zyvex Corporation, Richardson, Texas, Document: KZOO-ZZAN-001a, 2004.

"KZ100 Nanomanipulator System", Zyvex Corporation, Richardson, Texas, Document: KZ00-ZZDS-001c, 2004.

"SRAM Probing with Multiscan AFP", MultiProbe, Inc., Santa Barbara, California, Mulitprobe Movie, 2004.

Tuck, et al., "Powering MEMS Devices Using the S100 Nanomanipulator System", Zyvex Corporation, Richardson, Texas, Document: S1PM-ZZAN-001a, 2004.

"Zyvex A 100 Assembly System", Zyvex Corporation, Richardson, Texas, Document: A100-ZZDS-001c, 2004.

"Zyvex F100 Nanomanipulator System", Zyvex Corporation, Richardson, Texas, Document: F100-ZZDS-001c, 2004.

"Zyvex Mdriver 1000 MEMS Driving Station", Zyvex Corporation, Richardson, Texas, Document: ZMDR-ZZDS-001a, 2004.

"Zyvex NanoSharp Probes", Zyvex Corporation, Richardson, Texas, Document: ZPRB-ZZDS-001c, 2004.

"Zyvex Nanosolve Additives", Zyvex Corporation, Richardson, Texas, Document: ZZPN-ZZDS-001c, 2004.

"Zyvex Nanosolve Additives for Epoxies", Zyvex Corporation, Richardson, Texas, Document: EPOX-ZZDS-001a, 2004.

"Zyvex Nonosolve Additives for Polyurethane", Zyvex Corporation, Richardson, Texas, Document: ZNAP-ZZDA-001c, 2004.

"Zyvex S100 Nanomanipulator System", Zyvex Corporation, Richardson, Texas, Document: S100-ZZDS-001c, 2004.

International Preliminary Examination Report PCT/US03/16695, dated Sep. 03, 2004.

International Preliminary Examination Report PCT/US03/16750, dated Sep. 03,2004.

International Search Report/Written Opinion PCT/US2004/031482, dated Mar. 18, 2005.

European Patent Application No. 03734223.5 Search Report dated Feb. 6, 2006.

European Patent Application No. 03736728.1 Search Report dated Feb. 8, 2006.

European Patent Application No. 05251070.8 Search Report dated May 3, 2006.

"NanoEffector Tools", Zyvex Corporation, http://www.zyvex.com/Products/Grippers_Features.html.

"Processing Material In Electron Microscopes: Nanomanipulation With Several D.O.F." http://www.nanomotor.de/aa_processing.htm.

"SEM-Manipulators," http://www.nanomotor.de/pdf/Compare_e_lo.PDF.

Akazawa, "Bistable Si Growth Conditions on Ge(100) in Synchrotron-Radiation-Excited Atomic Layer Epitaxy from SiH2CI2", J. Appl. Phys. 81 (7), Apr. 1, 1997, pp. 3320-3322.

Akazawa, "Characterization of Self-limiting SiH2CI2 chemisorption and photon-stimulated desorption as elementary steps for Si atomic-layer epitaxy", NTT LSI Lab., Kanagawa, Japan, Physical Review B: Condensed Matter (1996), 54 (15), pp. 10917-10926.

Beck et al., "Ultrahigh Vacuum Instrument That Combines Variable-Temperature Scanning Tunneling Microscopy with Fourier Transform Infrared Reflection-Absorption Spectroscopy for Studies of Chemical Reactions at Surfaces," Rev. Sci. Instrum. 73(3), Mar. 2002, pp. 1267-1272.

Bergander et al., "A Testing Mechanism and Testing Procedure for Materials in Inertial Drives", IEEE MHS, pp. 213-218, Nagoya, Oct. 20-22, 2002.

Bergander et al., "Development of Miniature Manipulators for Applications in Biology and Nanotechnologies", proceeding of Workshop "Microrobotics for Biomanipulation", pp. 11-35, IEEE IROS 2003, Oct. 27-31, 2003, Las Vegas, USA.

Bergander et al., "Integrated Sensors for PZT Actuators Based on Thick-Film Resistors", IEEE MHS, pp. 181-186, Nagoya, Oct. 20-22, 2002.

Bergander et al., "Micropositioners for Microscopy Applications based on the Stick-Slip Effect", MHS 2000, Nagoya, pp. 213-216, Oct. 22-25, 2000.

Bergander et al., "Monolithic Piezoelectric Push-pull Actuators for Inertial Drives", IEEE MHS, pp. 309-316, Nagoya, Oct. 19-22, 2003.

Bergander et al., "Performance Improvements for Stick-Slip Positioners", IEEE MHS, pp. 59-66, Nagoya, Oct. 19-22, 2003.

Bergander et al., "Micropositioners for Microscopy Applications and Microbiology Based on Piezoelectric Actuators", Journal of Micromechatronics, vol. 2, No. 1, pp. 65-76, 2003.

Bergander, "Control, Wear Testing & Integration Of Stick-Slip Micropositioning", these no 2843, EPFL, Lausanne, Switzerland, 2003.

Binnig et al., "Single-tube three-dimensional scanner for scanning tunneling microscopy", Rev. Sci. Instrum. 57(8), Aug. 1986, pp. 1688-1689.

Blackford et al., "A vertical/horizontal two-dimensional piezoelectric driven inertial slider micropositioner for cryogenic applications", Rev. Sci. Instrum. 63(4), Apr. 1992, pp. 2206-2209.

Bleuler et al., "Applications of microrobotics and microhandling" in RIKEN Review No. 36 (Jun., 2001): Focused on Science and Technology in Micro/Nano Scale, pp. 26-28.

Breguet et al., "New Designs For Long Range, High Resolution, Multi-Degrees-Of-Freedom Piezoelectric Actuators", ACTUATOR'98, Breman, Germany, pp. 198-201, Jun. 17-19, 1998.

Breguet et al., "Stick and Slip Actuators: design, control, performances and applications", International Symposium on Micromechatronics and Human Science, Nagoya, Japan, pp. 89-95, Nov. 25-28, 1998.

Breguet, "Stick and Slip Micro-Robots", Institut de Systemes Robotiques (ISR), Jan. 14, 1999.

Co et al., "Iso-splatting: A Point-Based Alternative to Isosurface Visualization", Computer Graphics and Applications, 2003. Proceedings 11th Pacific Conference on Oct. 8-10, 2003, Piscataway, NJ, IEEE, Oct. 8, 2003, pp. 325-334.

Codourey et al., "High Precision Robots for Automated Handling of Micro Objects", Seminar on Handling and Assembly of Microparts, Vienna, Nov. 1994.

Colclough, "A fast high-voltage amplifier for driving piezoelectric positioners", Rev. Sci. Instrum. 71(11), Mar. 2000, pp. 4323-4324.

Danuser et al., "Manipulation of Microscopic Objects with Nanometer Precision: Potentials and Limitations in Nano-Robot Design".

Driesen et al., "Energy Consumption of Piezoelectric Actuators for Inertial Drives", IEEE MHS, pp. 51-58, Nagoya, Oct. 19-22, 2003.

Eigler et al., "Positioning Single Atoms with a Scanning Tunnelling Microscope", Nature, vol. 344, Apr. 5, 1990, pp. 524-526.

European Patent Application Number 05251070.8 Search Report dated Jun. 27, 2005.

Frohn et al., "Coarse Tip Distance Adjustment and Positioner for a Scanning Tunneling Microscope", Rev. Sci. Instrum. 60 (6), Jun. 1989, pp. 1200-1201.

FuturePundit, "Nanopore Technology: Sequence your DNA in Two hours!", Sep. 4, 2002, http://www.futurepundit.com/archives/000017.html.

Hasunuma et al., "Gas-Phase-Reaction-Controlled Atomic-Layer Epitaxy of Silicon", J. Vac. Sci. Technol. A16 (1998) 679.

Hersam et al., "Silicon-Based Molecular Nanotechnology", Nanotechnology 11, (2000), pp. 70-76.

Hinze, "Memo Functions, Polytypically!", Institut fur Informatik III, University Bonn, Bonn Germany, Jul. 2000.

IBM Research Press Solutions, "IBM Scientists Build World's Smallest Operating Computing Circuits", San Jose, CA, Oct. 24, 2002.

Imai et al., "Atomic layer epitaxy of silicon by gas confinement method", Department Physical Electronics, Tokyo Institute Technology, Tokyo, Japan, Transactions of the Materials Research Society of Japan (1994), 19A (Superconductors, Surfaces and Superlattices), pp. 145-148.

Ishida et al., "Growth temperature window and self-limiting process in sub-atomic-layer Epitaxy", Faculty Technology, Tokyo University Agriculture and Technology, Koganeri, Japan. Japanese Journal of Applied Physics, Part 1: (1996), 35(7), pp. 4011-4015.

Klocke Nanotechnik, "Manipulators: Universal Tools with 1 Nanometer Resolution," http://www.nanomotor.de/p_nanomanipulator.htm.

Langen et al., "Stick-slip actuators for micromachining of glass", International Conference on Micromechatronics for Information and Precision Equipment, Tokyo, Japan, pp. 261-264, Jul. 20-23, 1997.

Lyding et al., "Variable-temperature scanning tunneling microscope", Rev. Sci. Instrum. 59 (9), Sep. 1998, pp. 1897-1902.

Matsuyama et al., "Hetero atomic-layer epitaxy of Ge on Si(100)", Japanese Journal of Applied Physics, Part 1, vol. 39, No. 5A, May 2000, pp. 2536-2540.

Meller et al., "Voltage-Driven DNA Translocations through a Nanopore", Physical Review Letters, vol. 86, No. 15, Apr. 9, 2001, pp. 3435-3438.

Moller et al., "Tunneling Tips Imaged by Scanning Tunneling Microscopy", J. Vac. Sci. Technol. A 8 (1), Jan./Feb. 1990, pp. 434-437.

Mugele et al., "New Design of a variable-temperature ultrahigh vacuum scanning tunneling microscope", Rev. Sci. Instrum. 69(4), Apr. 1998, pp. 1765-1769.

Ott et al., "Al2O3 thin film growth on Si (100) using binary reaction sequence chemistry", Thin Solid Films 292 (1997) 135-144.

Parker et al., "Exploiting Self-Similarity in Geometry for Voxel Based Solid Modeling", Proc Symp Solid Model Appl; Proceedings of the Symposium on Solid Modeling and Applications 2003, Jun. 2003 (Jun. 2003), pp. 157-166.

Pérez et al, "Modelling, characterisation and implementation of a monolithic piezo actuator (MPA) of 2 and 3 degrees of freedom (DOF)", Actuator 2002, Bremen, Germany, Jun. 10-12, 2002.

Pérez et al., "Monolithic piezo-actuators: modeling, validation in the laboratory and optimisation of working conditions", ACTUATOR 2000, pp. 49-52, Bremen, Germany, Jun. 19-21, 2000.

Physik Instrumente, Theory and Applications of Piezo Actuators and PZT NanoPositioning Systems, www.physikinstrumente.com/tutorial, 2001.

Pi, "Basic Introduction to Nano-Positioning with Piezoelectric Technology", http/www.pi.ws, pp. 4/9-4/14.

Piezo Brochure, "Ultra Sonic Transducers & Crystals".

Pohl, "Dynamic Piezoelectric Translation Devices", Rev. Sci. Instrum., 58(1), Jan. 1987, pp. 54-57.

Popinet, "Gerris: a Tree-Based Adaptive Solver for the Incompressible Euler Equations in Complex Geometries", Journal of Computational Physics Academic Press USA, vol. 190, No. 2, Sep. 2003.

Renner et al., "A vertical piezoelectric inertial slider", Rev. Sci. Instrum. 61 (3), Mar. 1990, pp. 965-967.

Ritala et al., "Atomic Layer Epitaxy - a valuable tool for nanotechnology?", Nanotechnology V10 1999 pp. 19-24.

Rusinkiewicz et al., "Qspalt: A Multiresolution Point Rendering System for Large Meshes", Computer Graphics Proceedings, Annual Conference Series, 2000, pp. 343-352.

Satoh et al., "Atomic-layer epitaxy of silicon on (100) surface", Japanese Journal of Applied Physics, Part 1: Regular Papers and Short Notes and Review Papers v 39 n 10 Oct. 2000, pp. 5732-5736.

Shim et al., "Piezo-driven Metrological Multiaxis Nanopositioner", Rev. Sci. Instrum., 72(1); Nov. 2001, pp. 4183-4187.

Sugahara et al., "Modeling of silicon atomic-layer-epitaxy", Department of Physical Electronics, Tokyo Institute of Technology, Applied Surface Science (1996), 107 (Proceedings of the Third International Symposium on Atomically Controlled Surfaces and Interfaces, 1995), pp. 161-171.

Tu et al., "The Etree Library: A System for Manipulating Large Octrees on Disk", School of Computer Science, Pittsburgh, PA Jul. 2003.

Udeshi et al., "Memulator: A Fast and Accurate Geometric Modeling, Visualization and Mesh Generation for 3D MEMS Design and Simulation," Nanotech 2003, vol. 2, Technical Proceedings of the 2003 Nanotechnology Conference and TradeShow.

Udeshi, "Tetrahedral Mesh Generation from Segmented Voxel Data", 12th International Meshing Roundtable, Sep. 14-17, 2003.

Wildoer et al., "Scanning Tunneling Microscope Tip as a Positionable Contact: Probing a Josephson-Junction Array at Subkelvin Temperatures", J. Vac. Sci. Technol. B 16(5), Sep./Oct. 1998, pp. 2837-2840.

Yakimov, "Vertical Ramp-Actuated Inertial Micropositioner with a Rolling-Balls Guide", Rev. Sci. Instrum. 68 (1), Jan. 1997, pp. 136-139.

Zesch et al., "Inertial Drives for Micro-and Nanorobots: Two Novel Mechanims" Swiss Federal Institute of Technology.

Zesch, "Multi-Degree-of-Freedom Micropositioning Using Stepping Principles," Dissertation submitted to the Swiss Federal Institute of Technology, Zurich, 1997.

* cited by examiner ent. During the scanning process, the detector receives fewer electrons from depressions in the surface, and therefore lower areas of the surface appear darker in the resulting image. SEMs can provide a magnification of up to about two hundred thousand, possibly higher.

A focused ion beam (FIB) system is similar to a scanning electron microscope, except that instead of employing an electron beam, a beam of ions is scanned across the sample. The ion beam is ejected from a liquid metal ion source (e.g., gallium) with a spot size that is usually less than about 10 nm. FIB techniques can be employed in the preparation of samples for subsequent examination by a TEM or other electron microscope.

FIB specimens prepared for TEM are often manufactured by the "lift-out" method to provide a rapid means of preparing an electron transparent cross-section from a specific site of interest. In the lift-out method, a relatively large bulk sample can be inserted into the FIB chamber such that a specimen can be created from the surface of the sample. The specimen is then "lifted out" by the use of an electrostatic probe, which retrieves the sample from its trench and deposits the sample on an examination grid.

However, it can be difficult to accurately position and/or orient the retrieved sample with the electrostatic probe. For example, because the sample is temporarily adhered to the probe merely by electrostatic forces, the sample is not positively secured and may dislodge and/or become contaminated or destroyed. Consequently, an examination grid to which the sample is adhered or welded may be required. Such processes permit examination of the sample in only a single orientation, possibly requiring examination of multiple samples to adequately examine a substrate or substrate region.

METHOD, SYSTEM AND DEVICE FOR MICROSCOPIC EXAMINATION EMPLOYING FIB-PREPARED SAMPLE GRASPING ELEMENT

CROSS-REFERENCE/RELATED APPLICATIONS

The present application is related to and claims the benefit of the filing date of U.S. Provisional Application No. 60/505,026, filed Sep. 23, 2003, entitled "METHOD, SYSTEM AND DEVICE FOR MICROSCOPIC EXAMINATION EMPLOYING FIB-PREPARED SAMPLE GRASPING ELEMENT," by Skidmore, et al, the disclosure of which is hereby incorporated in its entirety herein.

The present application is also related to and claims the benefit of the filing date of U.S. Provisional Application No. 60/546,840, filed Feb. 23, 2004, entitled "AUTOMATED AND SEMI-AUTOMATED PROBING IN A CHARGED PARTICLE BEAM DEVICE," by Baur, et al, the disclosure of which is hereby incorporated in its entirety herein.

The present application is also related to: (1) U.S. patent application Ser. No. 10/173,542, filed Jun. 17, 2002, entitled "MANIPULATION SYSTEM FOR MANIPULATING A SAMPLE UNDER STUDY WITH A MICROSCOPE" by Dyer, et al.; and (2) U.S. patent application Ser. No. 10/173,543, filed Jun. 17, 2002 entitled "MODULAR MANIPULATION SYSTEM FOR MANIPULATING A SAMPLE UNDER STUDY WITH A MICROSCOPE" by Yu, et al.; the disclosures of which are hereby incorporated in their entirety herein.

The present application is also related to: (1) U.S. patent application Ser. No. 11/064,127, filed Feb. 23, 2005, entitled "AUTOMATED CHARGED PARTICLE BEAM DEVICE PROBING AND OPERATIONS" by Stallcup, et al.; (2) U.S. patent application Ser. No. 11/063,692, filed Feb. 23, 2005, entitled "PROBE CURRENT IMAGING" by Baur et al.; and (3) Ser. No. 11/064,131, filed Feb. 23, 2005, entitled "PROBE TIP PROCESSING" by Stallcup et al.

This invention was made with the United States Government support under 70NANB1H3021 awarded by the National Institute of Standards and Technology (NIST). The United States Government has certain rights in the invention.

BACKGROUND

Electron microscope equipment is often required to examine and perform manipulation of micro- and nano-scale objects. In general, electron microscopes employ a beam of electrons to irradiate a sample under study, wherein the wavelength of the electron beam is much smaller than the wavelength of light used in optical microscopes. Modern electron microscopes can view details at the atomic level with sub-nanometer resolution (e.g., 0.1 nm resolution) at a magnification of up to about one million. Electron microscopes and others which may be similarly employed include atomic force microscopes, scanning probe microscopes, scanning tunneling microscopes, near field optical scanning microscopes and transmission electron microscopes, among others.

A scanning electron microscope (SEM) is another type of electron microscope. In an exemplary SEM, a beam of electrons is focused to a point and scanned over the surface of the specimen. Detectors collect the backscattered and secondary electrons reflected or otherwise originating from the surface and convert them into a signal that is used to produce a realistic, three-dimensional image of the speci-

BRIEF DESCRIPTION OF THE DRAWINGS

Aspects of the present disclosure are best understood from the following detailed description when read with the accompanying figures. It is emphasized that, in accordance with the standard practice in the industry, various features may not be drawn to scale. In fact, the dimensions of the various features may be arbitrarily increased or reduced for clarity of discussion.

DETAILED DESCRIPTION

Figure 1:
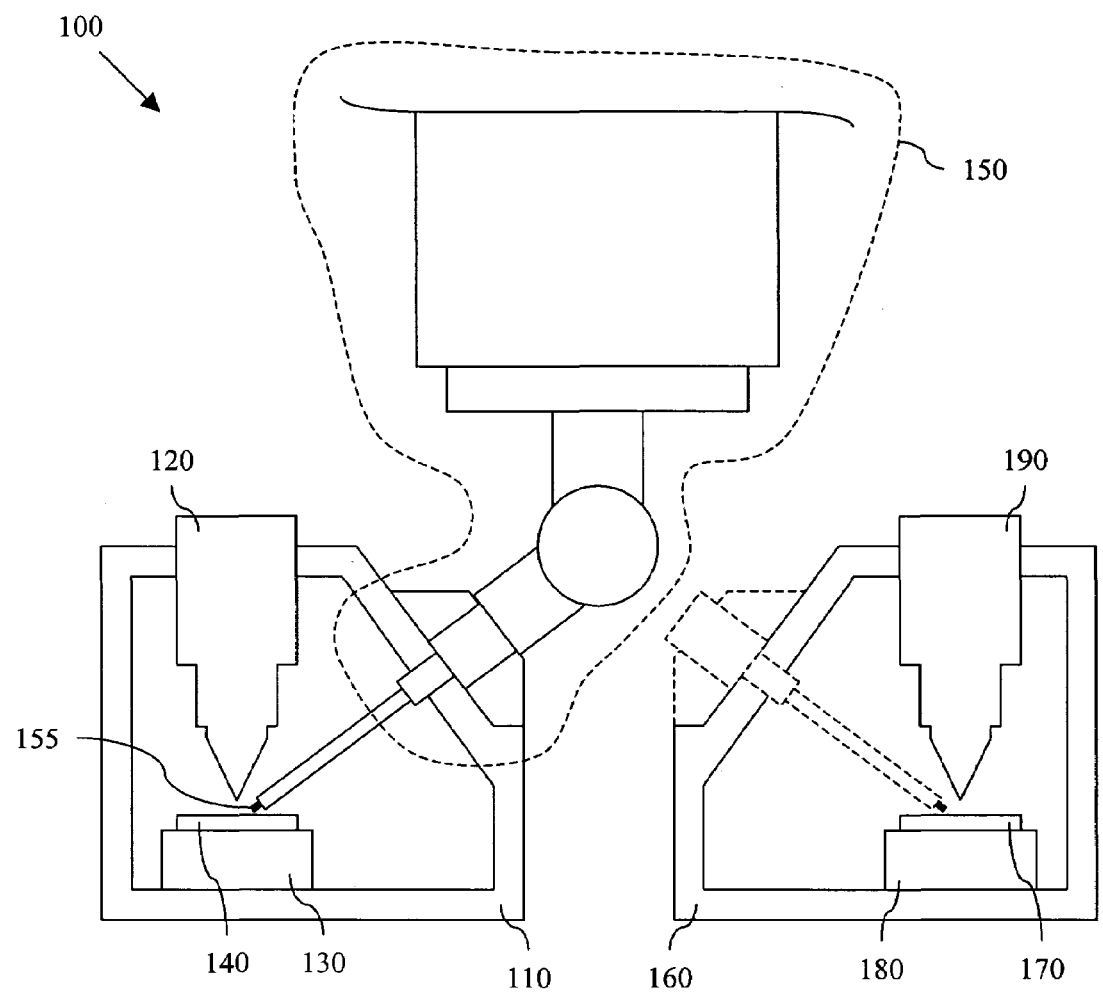
FIG. 1 is a schematic view of at least a portion of one embodiment of a system for microscopic examination according to aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Referring to FIG. 1, illustrated is a sectional view of at least a portion of one embodiment of a microscopic examination system 100 according to aspects of the present disclosure. The system 100 may include an FIB chamber 110 housing focused-ion-beam (FIB) means 120. The chamber 110 may also enclose a stage 130, such as may employed to support a substrate 140 to be examined by electron microscopy after FIB preparation of a sample, among other types of stages. The FIB chamber 110 may be a conventional or future-developed vacuum chamber or other type of chamber in which FIB procedures may be performed. The FIB means 120 may include conventional or future-developed apparatus for performing FIB procedures on the substrate 140, such as to prepare a sample of the substrate 140 for examination. For example, the FIB means 120 may include an ion source for generating an ion beam, as well as an ion beam optical system for irradiating the ion beam to a prescribed position. The stage 130 may be configured to position and orient the substrate 140 in up to 6 degrees-of-freedom relative to the chamber 110 and/or the FIB means 120.

The system 100 also includes a handling assembly 150 or other assembly, orientation and/or manipulation tool which may be employed, for example, to transport an FIB-prepared sample between the FIB chamber 110 and an electron microscopy chamber 160. The handling assembly 150 may be detachably coupled to either the FIB chamber 110 or the electron microscopy chamber 160, although the handling assembly may also be a free-standing apparatus. The handling assembly 150 includes a grasping element 155 configured to interface with an FIB-prepared sample. In some embodiments, the handling assembly 150, or portions or functions thereof, may be substantially enclosed within a chamber in which it is employed, such as the FIB chamber 110 and/or the microscopy chamber 160. For example, a positioning system or other type of manipulator may compose at least a portion of the handling assembly 150 and may be enclosed within the chamber in which a sample is manipulated.

The system 100 may also include more than one handling assembly 150, each of which may include one or more grasping elements 155. Each grasping element 155 may also be configured to interface with one or more FIB-prepared samples. As such, multiple samples may be prepared and/or manipulated, whether in series or in parallel, possibly via automation, as described further below. Where more than one handling assembly 150 or grasping element 155 is employed, each handling assembly 150 may or may not be substantially similar, and each grasping element 155 may or may not be substantially similar.

The grasping element 155 may also be configured to position and/or orient an FIB-sample in up to 6 degrees-of-freedom, such as to position an FIB-prepared sample on an examination grid 170 in the electron microscopy chamber 160, or to secure an FIB-prepared sample in the electron microscopy chamber 160 during examination, possibly in the absence of the examination grid 170. The grasping element 155 may be activated to grasp an FIB-prepared sample, such as by electrostatic, thermal, and/or piezoelectric activation of the grasping element 155. Alternatively, or additionally, the grasping element 155 may be de-activated to grasp an FIB-prepared sample. That is, the grasping element 155 may be configured to grasp an FIB-prepared sample in a power-on state and release the FIB-prepared sample in a power-off state, to grasp an FIB-prepared sample in a power-off state and release the FIB-prepared sample in a power-on state, to grasp an FIB-prepared sample in a power-on state and release the FIB-prepared sample in a power-on state, or to grasp an FIB-prepared sample in a power-off state and release the FIB-prepared sample in a power-off state.

The handling assembly 150, and possibly the grasping element 155, may be hand-operated and/or robotics-operated (automated), such that one or more procedural steps performed during sample preparation in the FIB chamber 110, sample transfer to the electron microscopy chamber 160, and/or sample examination in the electron microscopy chamber 160 may be performed with little or no human interaction once such procedural steps are initiated. Some procedural steps may also be initiated automatically, with little or no human interaction, by previous procedural steps.

The electron microscopy chamber 160 may be a conventional or future-developed vacuum chamber or other type of chamber in which electron microscopy procedures may be performed. The electron microscopy chamber 160 may include a stage 180 for supporting the examination grid 170 or, if no examination grid 170 is employed, for supporting an FIB-prepared sample and/or for cooperating with the handling assembly 150 to position and orient an FIB-prepared sample during examination. The electron microscopy chamber 160 also includes examination means 190 for examining an FIB-prepared sample. In one embodiment, the examination means 190 includes a transmission electron microscope (TEM). Of course, the examination means 190 may include other microscopy apparatus, including but not limited to a scanning electron microscope (SEM), an atomic force microscope, a scanning probe microscope, a scanning tunneling microscope (STM), or a near field optical scanning microscope the examination means 190 may also include examination means other than or in addition to an electron microscope, such as ion or optical microscopes. However, merely for the sake of simplicity, reference herein to any microscopy apparatus or device may be to an electron microscopy device, although such reference is intended to also include other microscopy devices, such as ion or optical microscopes. The examination means 190 may also include more than one microscopy apparatus. For example, the electron microscopy chamber 160 and/or the system 100 may include multiple chambers each employed for one or more steps in an examination process, such that one or more chambers may be employed for examination and/or further sample preparation steps.

In one embodiment of operation of the system 100, the substrate 140 to be examined is oriented in the FIB chamber 110, perhaps by manipulation of the stage 130 and/or the handling assembly 150. Thereafter, conventional or future-developed FIB processes are performed to define a sample from the substrate 140 for subsequent examination. The sample is then grasped, engaged, secured, or otherwise captured (hereafter collectively referred to as "captured") by the grasping element 155 by hand operation and/or robotic operation, and subsequently removed from the FIB chamber 110 by hand operation and/or robotic operation. The handling assembly 150 and grasping element 155 then transfer the FIB-prepared sample to the electron microscopy chamber 160 and orient the FIB-prepared sample for examination by the electron microscopy means 190. The transfer and/or orientation of the FIB-prepared sample may be hand-operated or robotics-operated (automated).

The FIB-prepared sample may remain captured by the grasping element 155 during the examination. In another embodiment, the handling assembly 150 and grasping element 155 position and orient the FIB-prepared sample on the examination grid 170 prior to examination, such that the FIB-prepared sample is released from the grasping element 155 prior to the examination. The handling assembly 150 and grasping element 155 may also or alternatively position and/or orient the FIB-prepared sample on the examination grid 170 prior to placement in the electron microscopy chamber 160, wherein the examination grid 170 is thereafter positioned and/or oriented in the electron microscopy chamber 160 after the FIB-prepared sample is released from the grasping element 155.

Operation of the system 100 may not require removing the FIB-prepared sample from the FIB chamber prior to examination by electron microscopy. For example, a single chamber (or multi-chambered tool) may include both the FIB means 120 and the electron microscopy means 190. Consequently, the FIB-prepared sample may merely be transported between work areas of the FIB and electron microscopy means 120,190 and properly oriented by the handling assembly 150 and grasping element 155, or the FIB-prepared sample may substantially remain stationary while FIB means 120 is repositioned away from the sample and the electron microscopy means 190 is repositioned proximate the sample for examination.

In some embodiments, the examination grid 170 may include grasping means or other means for coupling or otherwise securing the sample, such as one or more latches, clamps, sockets, handles, combinations thereof, etc. Such grasping means may include and/or resemble one or more embodiments of the grasping elements described below. For example, in one embodiment, the examination grid 170 may include grasping means comprising two or more grasping members biased against each other or otherwise in close proximity or contacting, wherein the grasping members may have an elastic or biasable nature. In such an embodiment, the FIB-prepared sample may be urged to a position between the grasping members and released by the grasping element 155, such that the biasable nature of the examination grid 170 grasping members may secure the sample without requiring the sample to be welded or otherwise permanently affixed to the examination grid 170. The grasping members of the examination grid 170 may also have an inner or other profile corresponding to an outer or other profile of the FIB-prepared sample, such as may be configured to rigidize or otherwise improve or aid in the sample being secured relative to the examination grid 170, possibly in one or more predetermined positions.

Consequently, in some embodiments, the grasping element 155 may be employed to initially position the sample on the examination grid 170, release the sample, and subsequently re-grasp the sample to re-orient the sample and position the sample on the examination grid 170 in a new orientation. Similarly, in some embodiments, the grasping element 155 may be employed to initially position the sample on the examination grid 170, release the sample, and subsequently re-grasp the sample to transfer the sample to another examination and/or processing environment, such as an additional microscopy chamber.

Figure 2:
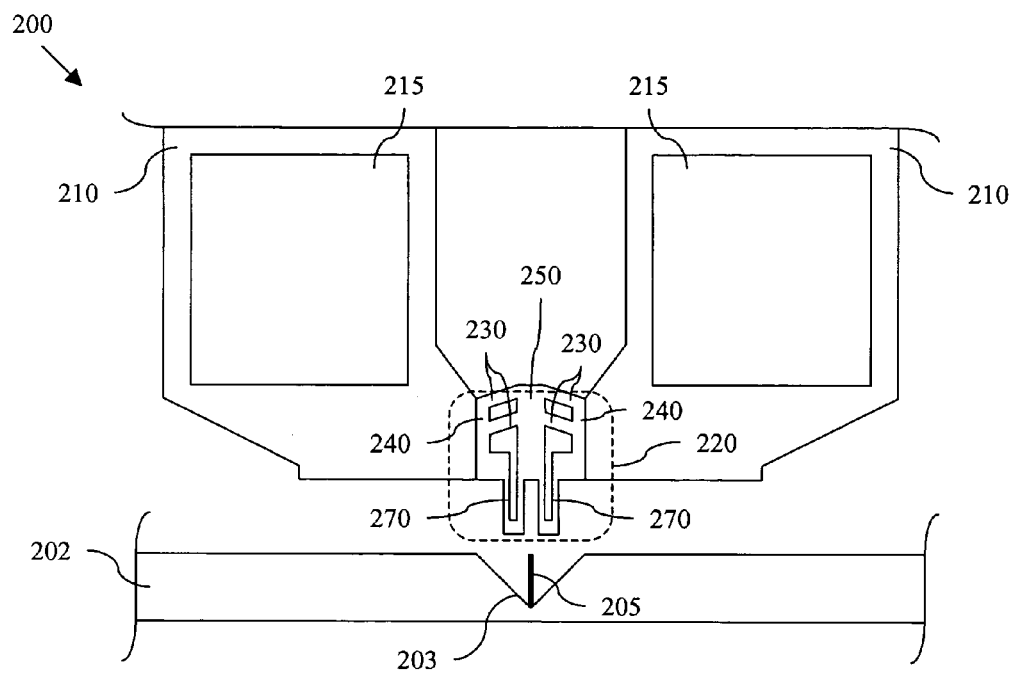
FIG. 2 is a schematic view of at least a portion of one embodiment of a grasping element according to aspects of the present disclosure.

Referring to FIG. 2, illustrated is a schematic view of at least a portion of one embodiment of a grasping element 200 according to aspects of the present disclosure. In one embodiment, the grasping element 200 may be employed in the system 100 shown in FIG. 1, such as in the role of the grasping element 155. The grasping element 200 may include a body 210 having bond pads 215 formed thereon or therein. The grasping element 200 also includes an actuator 220 for grasping a sample 205 prepared from a substrate 202, such as by FIB techniques. The actuator 220 includes one or more actuating members 230, which may be or include ribbon-shaped, rectilinear members and/or otherwise shaped members. Distal ends 240 of the actuating members 230 may be integral or otherwise coupled to the body 210. Proximate ends of the actuating members 230 may also be coupled to one another, perhaps by a spacer member 250. Alternatively, one or more of the actuating member 230 may substantially span the width of the actuator 220, possibly having an angled or arcuate concave profile (e.g., skewed toward a central portion of the body 210, as in FIG. 2) or an angled or arcuate convex profile (e.g., skewed away from a central portion of the body 210).

The grasping element 200 also includes grasping members 270 integral or coupled to the actuating members 230. The grasping members 270 are configured to secure the FIB-prepared sample 205 upon activation or deactivation of the grasping element 200. For example, the actuating members 230 may be configured to expand and contract in response to exposure to thermal energy. Such exposure may be achieved by employing a heat lamp, hot plate or oven. Localized heating may be also achieved with a laser device. In one embodiment, the actuating members 230 are configured to expand and contract in response to thermal energy generated by electrical current propagating along the actuating members 230. For example, the actuating members 230 or other portions of the grasping element 200 may comprise electrically resistive elements or material which increases in temperature in response to electrical current. Accordingly, the actuating members 230 may be directly or indirectly coupled to bond pads 215 or other means for interconnection with a current or voltage source.

In embodiments in which the grasping element 200 is activated or deactivated in response to resistive heating, the resistive elements which may provide such resistive heating within the actuator 220 may comprise lengths of resistive material, such as single crystal silicon, doped polysilicon and/or other conventional or future-developed materials which generate thermal energy in response to electrical current. The resistive elements may be located in or on the actuating members 230 or elsewhere in or on the grasping element 200 within a sufficiently short distance from the actuating members 230 such that the thermal energy dissipated by the resistive elements when the grasping element 200 is activated is sufficient to cause the actuating members 230 to expand and contract in response to the thermal energy.

The actuating members 230 may also or alternatively be configured to expand and contract in response to exposure to a bias voltage applied across the grasping members 270 or to the actuating members 230. Such a bias may be achieved by interconnection of the actuating members 230 or grasping members 270 with a voltage source, possibly employing the bond pads 215 as such an interconnection means. In one embodiment, the actuating members 230 may be configured to expand and/or contract other than in response to thermal energy, such that the actuating members 230 may not be thermally actuated, but may be actuated by other means. In one embodiment, the actuating members 230, or portions thereof, and/or support structure associated therewith, may comprise shape memory alloys, including those that may be activated electrically and/or thermally.

The actuating members 230 expand as they increase in temperature in response to the exposure to thermal energy. Although a variety of thermal expansion schemes are contemplated by the present disclosure (e.g., geometries, thermal expansion coefficients and corresponding directions of expansion), the illustrated embodiment depicts the actuating members 230 as having significantly more length than width or height. Thus, the exposure to thermal energy will cause the actuating members 230 to expand in length more than any other direction. However, because the ends 240 of the actuating members 230 are fixed, the expansion in the length of the actuating members 230 will cause them to buckle or translate toward a central portion of the body 210. Consequently, the midpoints of the actuating members 230 and the spacer member 250 will translate toward a central portion of the body 210. Because the midpoints of the actuating members 230 may all be skewed off-center in the same direction, the actuating members 230 may each buckle or translate in the same direction during expansion.

The subsequent translation of the spacer member 250 toward a central portion of the body 210 causes the angle between opposing sections of the actuating members 270 to decrease. Consequently, in addition to the spacer member 250 translating toward a central portion of the body 210, the grasping members 270 may also rotate inward, thereby grasping opposing sides of the FIB-prepared sample 205.

In one embodiment, the position of the grasping members 270 in the activated position, such as after positioning in response to exposure to thermal energy, may be a sample-released position. In such an embodiment, the grasping members 270 may secure the FIB-prepared sample 205 in a power-off condition. That is, the grasping members 270 may expand or separate from one another in response to thermal energy or other activation means, and contract to a closed position upon removal from the thermal energy or other activation means. Accordingly, the thermal energy or other activation means may only be required to initially position the grasping members 270 proximate the sample 205 prior to grasping the sample 205, such that the thermal energy need not be continuously applied while the FIB-prepared sample 205 is transported between chambers or tools or during positioning or orientation of the FIB-prepared sample 205 within a chamber or tool.

In one embodiment, the grasping element 200 may be manufactured as a micro-electro-mechanical (MEMS) device. For example, an insulating layer and one or more conductive layers may be successively stacked on a substrate. The body 210 and actuator 220 may be defined in the conductive layer by micromachining and/or conventional or future-developed etching processes, possibly employing a mask of photoresist or other materials. The bond pads 215 may be formed from the same conductive layers as the body 210, or the bond pads 215 may be defined in a second conductive layer over the conductive layer from which the body 210 is defined. The grasping element 200 also includes means for interfacing with a handling assembly, such as the handling assembly 150 shown in FIG. 1, although such interface means are not limited by the scope of the present disclosure. Such interfacing means may also be defined in the layer from which the body 210 is defined. The insulating layer may comprise undoped silicon, silicon dioxide, another oxide or electrically insulating materials, and the one or more conductive layers may comprise doped polysilicon, gold and/or other electrically conductive materials.

Figure 3:
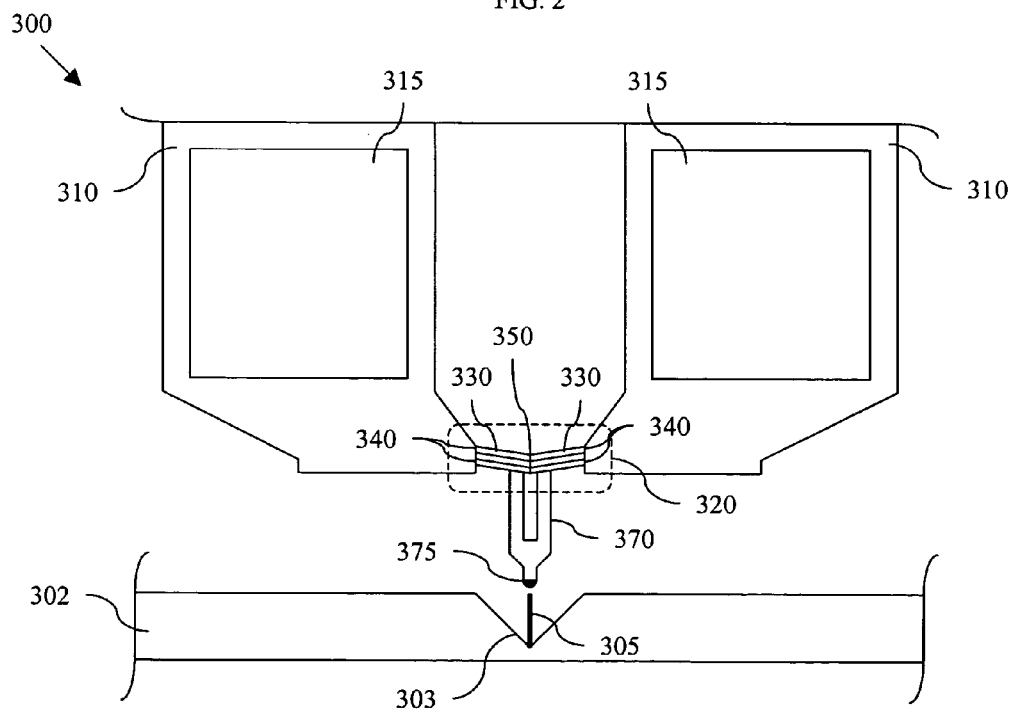
FIG. 3 is a schematic view of at least a portion of another embodiment of a grasping element according to aspects of the present disclosure.

Referring to FIG. 3, illustrated is a schematic view of at least a portion of another embodiment of a grasping element 300 according to aspects of the present disclosure. The grasping element 300 may be substantially similar in composition and manufacture to the grasping element 200 shown in FIG. 2, and may be employed in an electron microscopy system such as the system 100 shown in FIG. 1.

The grasping element 300 may include a body 310 having bond pads 315 formed thereon or therein. The grasping element 300 may also include an actuator 320 for capturing a sample 305 prepared from a substrate 302 by FIB techniques. The actuator 320 may include one or more actuating members 330, which may be or include ribbon-shaped, rectilinear members and/or otherwise shaped members. The ends 340 of the actuating members 330 may be integral or otherwise coupled to the body 310. The actuating members 330 may also be coupled to one another at or near their midpoints 350, perhaps by a spacer member. Moreover, the midpoints 350 may have a neutral position that is slightly offset or skewed towards or away from a central portion of the body 310. In the illustrated embodiment, the midpoints 350 are skewed away from a central portion of the body 310.

The grasping element 300 also includes a grasping member 370 integral or coupled to the actuating members 330. The grasping member 370 is configured to secure the FIB-prepared sample 305 upon activation or deactivation of the grasping element 300. For example, the grasping member 370 may comprise a compression bond end-effector 375 configured to interface with the FIB-prepared sample 305. Of course, the shape of the compression bond end-effector 375 is not limited to the substantially hemispherical or semicircular shape shown in FIG. 3, and may be otherwise shaped to interface with the FIB-prepared sample 305 to aid in removal of the sample 305 from the substrate 302. For example, the compression bond end-effector 375 may have an arcuate, angled or rectilinear concave shape, which may aid in guiding the compression bond end-effector 375 to the edge of the FIB-prepared sample 305.

The compression bond end-effector 375 may be or comprise a film or other surface treatment that is malleable, thermally conductive and/or electrically conductive to assist in bonding with the FIB-prepared sample 305. For example, the film may comprise gold, silver, indium, and/or other materials. A surface treatment or surface treated portion of the compression bond end-effector 375 may be, comprise, or result from one or more processes that modify a surface of the compression bond end-effector 375 or otherwise enhance bonding capability. Such films and/or surface treatments may employ nanotube structures or materials or other possibly textured compositions, which may provide inherent compliance and/or increase Van der Waals bonding forces.

The actuating members 330 may be configured to expand and contract in response to exposure to thermal energy. Such exposure may be achieved by employing a heat lamp, hot plate or oven. Localized heating may be also achieved with a laser device. In one embodiment, the actuating members 330 are configured to expand and contract in response to thermal energy generated by electrical current propagating along the actuating members 330 or other portions of the grasping element 300. For example, the actuating members 330 may comprise electrically resistive elements or materials which increase in temperature in response to electrical current. Accordingly, the actuating members 330 may be directly or indirectly coupled to bond pads 315 or other means for interconnection with a current or voltage source.

In embodiments in which the grasping element 300 is activated in response to resistive heating, the resistive elements which may provide such resistive heating within the actuator 320 may comprise lengths of resistive material, such as doped polysilicon and/or other conventional or future-developed materials which dissipate thermal energy in response to electrical current. The resistive elements may be located in or on the actuating members 330 or elsewhere in or on the grasping element 300 within a sufficiently short distance from the actuating members 330 such that the thermal energy dissipated by the resistive elements when the grasping element 300 is activated is sufficient to cause the actuating members 330 to expand and contract in response to the thermal energy. The actuating members 330 may also or alternatively be configured to expand and contract in response to exposure to a bias voltage applied to the actuating members 330. Such a bias may be achieved by interconnection of the actuating members 330 with a voltage source, possibly employing the bond pads 315 as such an interconnection means.

The actuating members 330 expand as they increase in temperature in response to the exposure to thermal energy. Although a variety of thermal expansion schemes are contemplated by the present disclosure (e.g., geometries, thermal expansion coefficients and corresponding directions of expansion), the illustrated embodiment depicts the actuating members 330 as having significantly more length than width or height. Thus, the exposure to thermal energy will cause the actuating members 330 to expand in length more than any other direction. However, because the ends 340 of the actuating members 330 are fixed, the expansion in the length of the actuating members 330 will cause them to buckle. Consequently, the midpoints 350 of the actuating members 330 will translate laterally. Because the midpoints 350 of the actuating members 330 may all be skewed off-center in the same direction, the actuating members 330 may each buckle in the same direction during expansion.

The translation of the midpoints 350 of the actuating members 330 away from a central portion of the body 310 causes the grasping member 370 to also translate away from a central portion of the body 310. Consequently, the compression bond end-effector 375 will contact the FIB-prepared sample 305. The compression bond end-effector 375 may bond with the FIB-prepared sample 305 merely by the force applied through the grasping member 370 by the expansion of the actuating members 330. However, bonding between the end-effector 375 and the FIB-prepared sample 305 may be assisted by exposure to acoustic and/or thermal energy. Such exposure to thermal energy may be as described above, wherein the exposure to and/or removal from thermal energy causes a mechanical and/or chemical bond to form between the end-effector 375 and the FIB-prepared sample 305. Exposure to acoustic energy may include the radiation of high frequency sound or pressure waves from a source located central to or remote from the grasping element 300.

In one embodiment, the position of the grasping member 370 shown in FIG. 3 may be a biased or activated position, such as after positioning in response to exposure to thermal energy. Accordingly, the thermal energy or other activation means may only be required to initially secure the FIB-prepared sample 305, such that the thermal energy or other activation means need not be continuously applied while the FIB-prepared sample 305 is transported between chambers or tools or during positioning or orientation of the FIB-prepared sample 305 within a chamber or tool.

In another embodiment, the grasping member 370 may be rigidly coupled to the body 310. In such embodiments, the grasping element 300 may not include the actuating member 330 or any other actuating component. That is, the grasping member 370 may be positioned in close proximity to or contacting the FIB-prepared sample 305 merely by positioning of the body 310. The grasping member 370 may subsequently be exposed to thermal energy, such as by conducting current through the grasping member 370, whereby the thermal energy may melt or catalyze a portion of the end-effector 375 or otherwise aid in bonding the grasping member 370 to the FIB-prepared sample 305. The FIB-prepared sample 305 may include a layer of material having substantial hardness, such as platinum or tungsten, to provide a hard surface against which the grasping member 370 may be pressed, such as during the formation of a compression bond between the grasping member 370 and the FIB-prepared sample 305. Thus, activating the grasping element 300 may comprise physically positioning the grasping element 300 in addition to, or alternatively to, exposing at least a portion of the grasping element 300 to thermal and/or other energy.

Figure 4A:
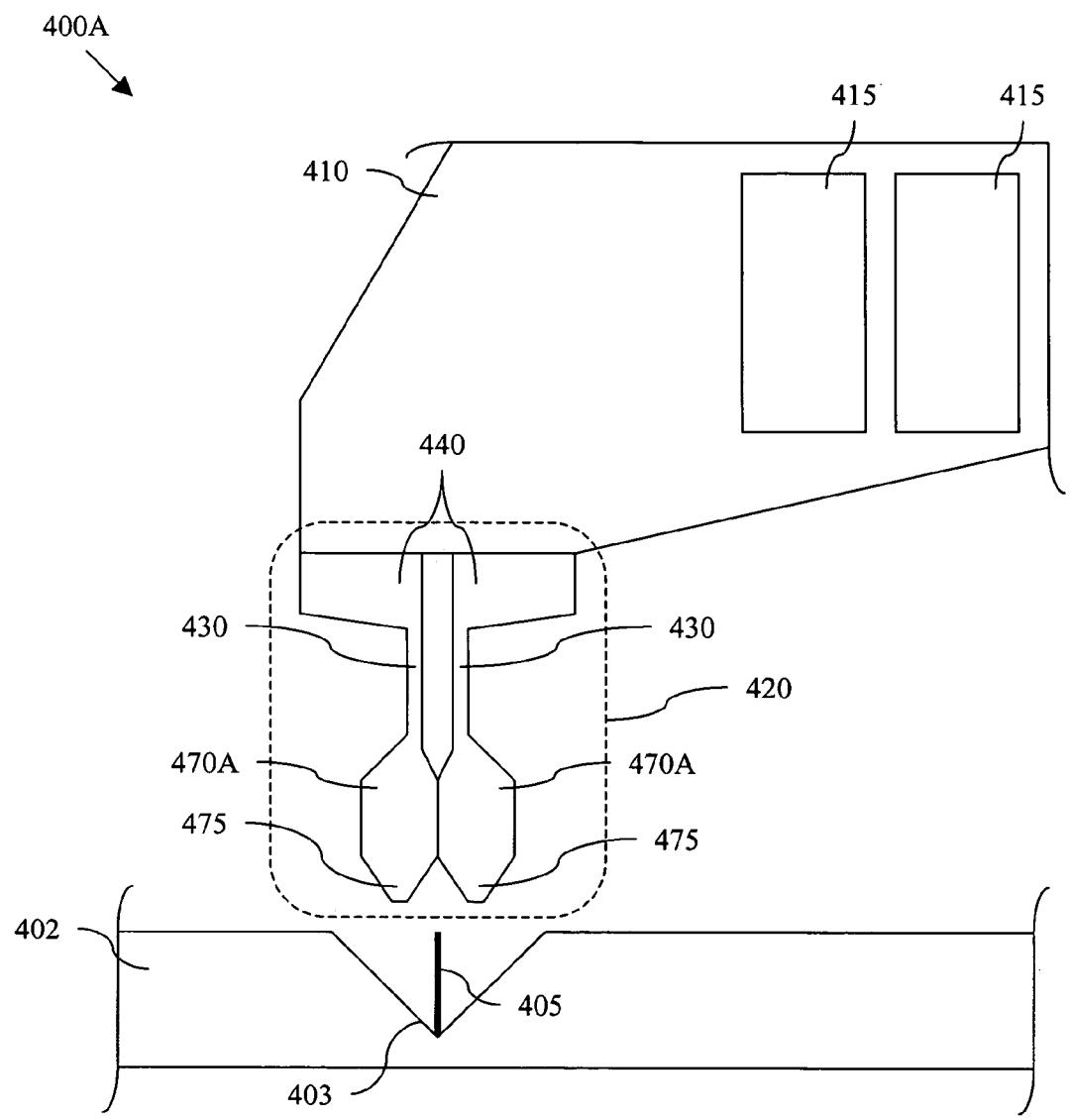
FIG. 4A is a schematic view of at least a portion of another embodiment of a grasping element according to aspects of the present disclosure.

Referring to FIG. 4A, illustrated is a schematic view of at least a portion of another embodiment of a grasping element 400A according to aspects of the present disclosure. The grasping element 400A may be substantially similar in composition and manufacture to the grasping element 200 shown in FIG. 2, and may be employed in an electron microscopy system such as the system 100 shown in FIG. 1.

The grasping element 400A may include a body 410 having bond pads 415 formed thereon or therein. The grasping element 400A also includes an actuator 420 for grasping a sample 405 prepared from a substrate 402, such as by FIB processes. The actuator 420 includes one or more actuating members 430, which may be or comprise ribbon-shaped, rectilinear members or otherwise shaped members. First ends 440 of the actuating members 430 may be integral or otherwise coupled to the body 410.

The actuating members 430 also include grasping members 470A at ends opposite the body 410. The grasping members 470A may be integral or coupled to the actuating members 430. The grasping members 470A are configured to secure the FIB-prepared sample 405 upon activation or deactivation of the grasping element 400A. For example, the grasping members 470A may comprise triangular tips 475 configured to fit around or otherwise correspond to the FIB-prepared sample 405. Also, or alternatively, the grasping members 470A may be configured to cooperate with, engage, fit into, or otherwise correspond to one or more holes, apertures, recesses, indentations, slots, trenches, or other openings 403 formed in the substrate 402 and/or the sample 405, such as during the FIB process. The shape of the tips 475 is not limited to the triangular or blunted triangular shape shown in FIG. 4A, and may be otherwise shaped to fit around the FIB-prepared sample 405 and/or in the opening 403 to grasp the sample 405 and remove the sample 405 from the substrate 402.

The actuating members 430 may be configured to expand and contract in response to exposure to thermal energy. Such exposure may be achieved by employing a heat lamp, hot plate or oven. Localized heating may be also achieved with a laser device. In one embodiment, the actuating members 430 are configured to expand and contract in response to thermal energy generated by electrical current propagating along the actuating members 430 or other portions of the grasping element 400A. For example, the actuating members 430 may comprise electrically resistive elements or material which increases in temperature in response to electrical current. Accordingly, the actuating members 430 may be directly or indirectly coupled to bond pads 415 or other means for interconnection with a current or voltage source.

In embodiments in which the grasping element 400A is activated in response to resistive heating, the resistive elements which may provide such resistive heating within the actuator 420 may comprise lengths of resistive material, such as doped polysilicon and/or other conventional or future-developed materials which generate thermal energy in response to electrical current. The resistive elements may be located in or on the actuating members 430 or elsewhere in or on the grasping element 400A within a sufficiently short distance from the actuating members 430 such that the thermal energy dissipated by the resistive elements when the grasping element 400A is activated is sufficient to cause the actuating members 430 to expand and contract in response to the thermal energy.

The actuating members 430 may also or alternatively be configured to expand and contract in response to exposure to a bias voltage applied across the grasping members 470A or to the actuating members 430. Such a bias may be achieved by interconnection of the actuating members 430 or grasping members 470A with a voltage source, possibly employing the bond pads 415 as such an interconnection means.

The actuating members 430 expand as they increase in temperature in response to the exposure to thermal energy. Although a variety of thermal expansion schemes are contemplated by the present disclosure (e.g., geometries, thermal expansion coefficients and corresponding directions of expansion), the illustrated embodiment depicts the actuating members 430 as having significantly more length than width or height. Thus, the exposure to thermal energy will cause the actuating members 430 to expand in length more than any other direction. The expansion of the actuating members 430 will cause the grasping members 470A to extend laterally away from the body 410. Consequently, the grasping members 470A will interface with the FIB-prepared sample 405. The interference of the FIB-prepared sample 405 and the sloped surfaces of the tips 475 will cause the grasping members to separate to the extent necessary that the grasping members 470A will at least partially slide over the edge of the FIB-prepared sample. Upon the removal of the grasping element 400A from the thermal energy exposure or other activation means, the grasping members 470A will be biased towards the neutral position shown in FIG. 4A, thereby grasping the sides of the FIB-prepared sample 405 and capturing the FIB-prepared sample 405 for subsequent translation, positioning and/or orienting.

In one embodiment, the actuating members 430 may be flexible members configured to grasp the FIB-prepared sample 405 without activation in response to thermal energy or other activation. For example, the actuating members 430 may be brought into close proximity with the FIB-prepared sample 405 and then pressed over the end of the sample 405. Because the actuating members 430 may be flexible members, they may separate in response to the FIB-prepared sample 405 being forced between the members 430. However, the flexible nature of the actuating members 430 may cause them to pinch or grasp the FIB-prepared sample 405 as they slide down the sides of the sample 405. Thereafter, the FIB-prepared sample 405 may be completely severed from the substrate 402, such that it remains captured only by its interference fit between the flexible actuating members 430. Thus, actuating the grasping element 400A may comprise physically positioning the grasping element 400A in addition to, or alternatively to, exposing the grasping element 400A to thermal energy, electrostatic energy, and/or piezoelectric driving energy or means.

Figure 4B:
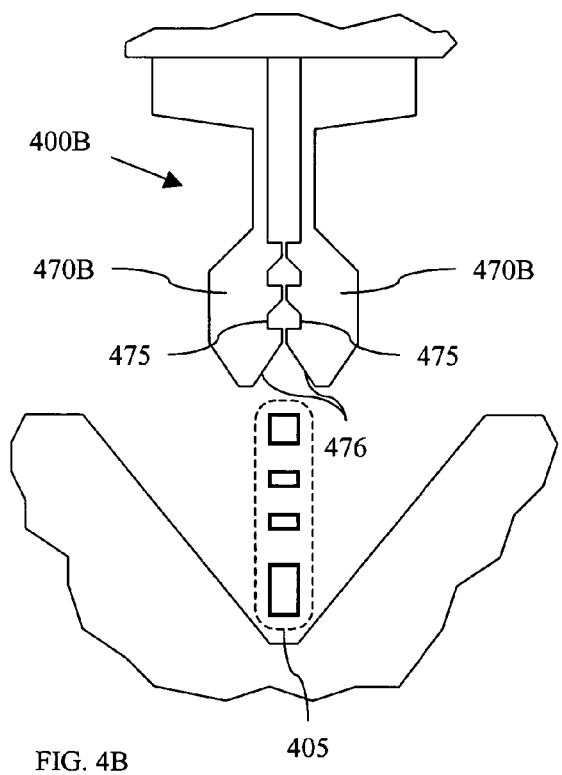
FIGS. 4B and 4C are schematic views of at least a portion of another embodiment of a grasping element according to aspects of the present disclosure.
Figure 4C:
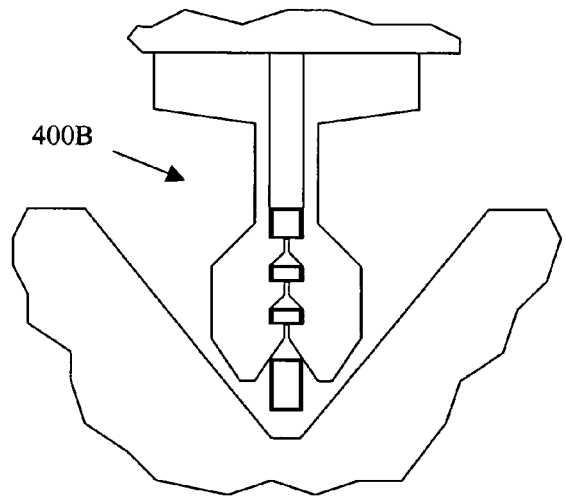

Referring to FIGS. 4B and 4C collectively, illustrated are schematic views of another embodiment of the grasping element 400A shown in FIG. 4A, herein designated by reference numeral 400B. The grasping element 400B may be substantially similar to the grasping element 400A except possibly as described below. Thus, as in the illustrated embodiment, the grasping element 400B includes grasping members 470B that are substantially similar to the grasping members 470A shown in FIG. 4A.

However, each of the grasping members 470B includes an inner profile 475 configured to engage, cooperate, or otherwise at least partially correspond to a profile of an FIB-prepared sample 405. For example, the inner profile 475 may have a castellated, serrated, saw-toothed, or otherwise undulating profile which corresponds to one or more recesses or openings 407 in the sample 405, such as in the embodiment shown in FIGS. 4B and 4C. Consequently, as the grasping element 400B is positioned over the sample 405, the inner profile 475 of the grasping element 400B may engage at least a portion of the sample 405, as shown in FIG. 4C. Of course, the cross-sectional shape of the sample 405 may not conform or resemble the substantially rectangular cross-section of the sample 405 shown in FIGS. 4B and 4C. Moreover, such FIB-prepared samples having a substantially non-rectangular cross-section may also be employed with other embodiments within the scope of the present disclosure, including those described above.

In some embodiments, the sample 405 may urge apart or otherwise deflect the grasping members 470B as the grasping element 400B is positioned over the sample 405. Consequently, some embodiments of the grasping members 470B may have angled, sloped, concave, convex, or otherwise shaped surfaces (e.g., surfaces 476) which may urge the grasping members 470 apart in response to contact with the sample, and/or may aid in guiding the grasping element 400B over the sample 405. The grasping members 470B may also be activated or deactivated as the grasping element 400B is positioned over the sample 405, such as by exposure to electrical and/or thermal energy and/or other activation means, including those described above.

Moreover, the grasping members 470B may not be mirror images of each other, as in the embodiment illustrated in FIGS. 4B and 4C and others herein. For example, only a first one of the grasping members 470B may have the inner profile 475 described above, which may substantially correspond to at least a portion of the profile of the sample 405, whereas the second grasping member may have a substantially planar profile or otherwise not mirror or correspond to the first grasping profile 475. In such embodiments, the profile of the second grasping member may also not correspond to any portion of the profile of the sample 405. Of course, such dissimilarity between the grasping members 470B of the grasping element 400B may also apply to other embodiments of grasping elements within the scope of the present disclosure.

Figure 4D:
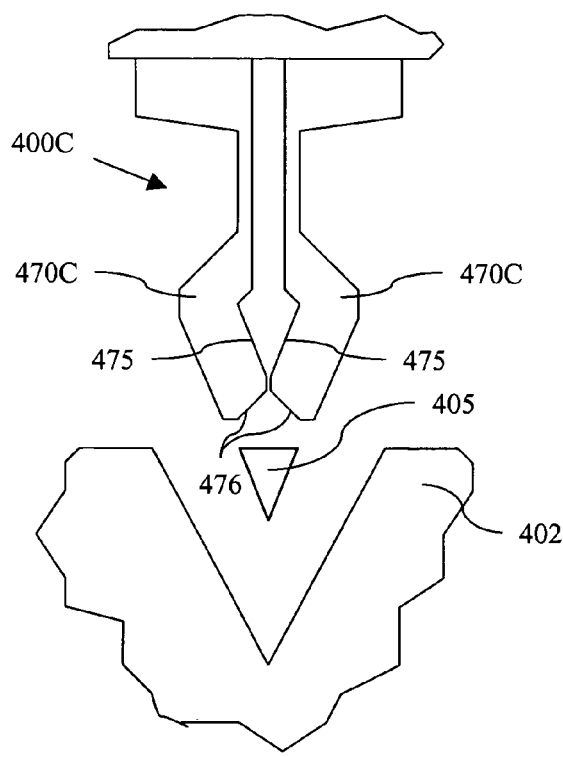
FIGS. 4D and 4E are schematic views of at least a portion of another embodiment of a grasping element according to aspects of the present disclosure.
Figure 4E:
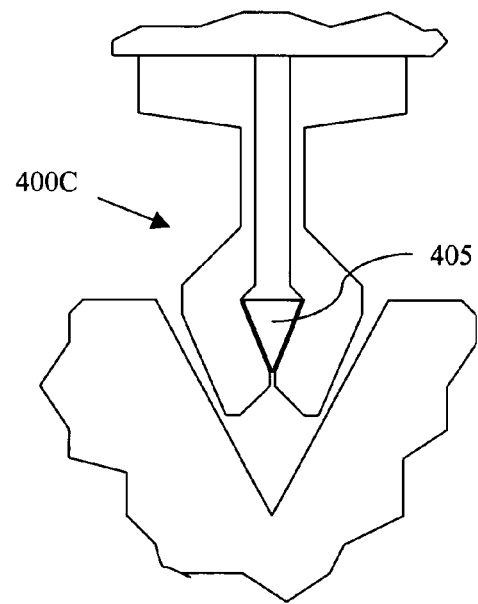

Referring to FIGS. 4D and 4E collectively, illustrated are schematic views of another embodiment of the grasping element 400A shown in FIG. 4A, herein designated by reference numeral 400C. The grasping element 400C may be substantially similar to the grasping element 400A except possibly as described below. Thus, as in the illustrated embodiment, the grasping element 400C includes grasping members 470C that are substantially similar to the grasping members 470A shown in FIG. 4A.

However, each of the grasping members 470C includes an inner profile 475 configured to engage, cooperate, or otherwise at least partially correspond to a profile of an FIB-prepared sample 405. FIGS. 4D and 4E also illustrate that the sample 405 may have a cross-sectional shape other than the substantially rectangular cross-section otherwise shown herein. For example, the sample 405 shown in FIGS. 4D and 4E has a substantially triangular-shaped cross-section. In other embodiments, the cross-section of the sample 405 may have other geometric shapes, including asymmetric or irregular shapes. However, regardless of the particular cross-sectional shape of the sample 405, the inner profile 475 of the grasping members 470C may substantially conform to, engage with, cooperate with, or otherwise correspond to the cross-sectional shape of the sample 405. In some embodiments, the correspondence between the inner profile 475 of the grasping members 470C and the cross-section of the sample 405 may be sufficient to allow the grasping element 400C to remove the sample 405 from the substrate 402 by tearing, ripping, breaking, fracturing, disuniting or otherwise compromising a tapered, necked, thinned, or other portion of the sample 405 connecting the sample 405 to the substrate 402, possibly by merely grasping the sample 405 and translating the grasping element 400C away from the substrate 402.

In some embodiments, the sample 405 may urge apart or otherwise deflect the grasping members 470C as the grasping element 400C is positioned over the sample 405. Consequently, some embodiments of the grasping members 470C may have angled, sloped, concave, convex, or otherwise shaped surfaces (e.g., surfaces 476) which may urge the grasping members 470 apart in response to contact with the sample, and/or may aid in guiding the grasping element 400B over the sample 405. The grasping members 470B may also be activated or deactivated as the grasping element 400B is positioned over the sample 405, such as by exposure to electrical and/or thermal energy and/or other activation means, including those described above.

Moreover, the grasping members 470B may not be mirror images of each other, as in the embodiment illustrated in FIGS. 4B and 4C and others herein. For example, only a first one of the grasping members 470B may have the inner profile 475 described above, which may substantially correspond to at least a portion of the profile of the sample 405, whereas the second grasping member may have a substantially planar profile or otherwise not mirror or correspond to the first grasping profile 475. In such embodiments, the profile of the second grasping member may also not correspond to any portion of the profile of the sample 405. Of course, such dissimilarity between the grasping members 470B of the grasping element 400B may also apply to other embodiments of grasping elements within the scope of the present disclosure.

Figure 5:
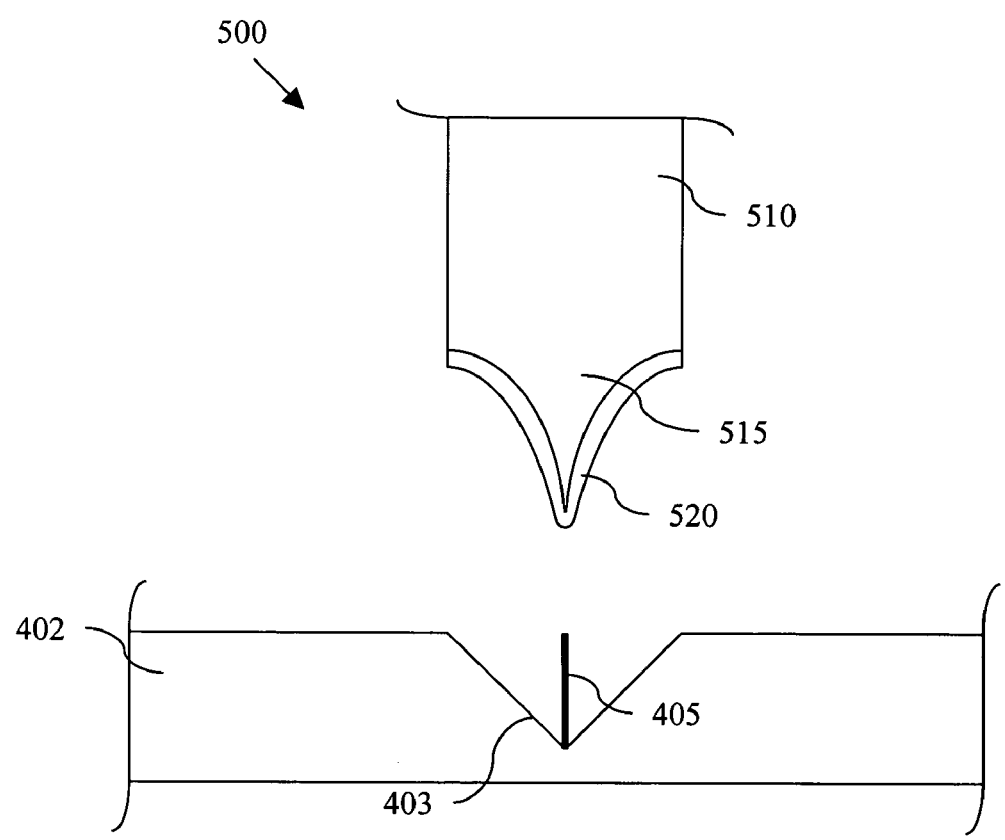
FIG. 5 is a schematic view of at least a portion of another embodiment of a grasping element according to aspects of the present disclosure.

Referring to FIG. 5, illustrated is a schematic view of at least a portion of another embodiment of a grasping element 500 constructed according to aspects of the present disclosure. The grasping element 500 may be employed in an electron microscopy system such as the system 100 shown in FIG. 1, and may otherwise may similar to the grasping elements described with respect to FIGS. 1–3 and 4A–4E.

The grasping element 500 includes a body 510 which, in one embodiment, substantially comprises a wire segment. The body 510 may comprise tungsten or other materials from which a probe may be formed from a wire segment. For example, the body may comprise a tungsten wire segment having an end 515 that is etched or otherwise formed into a probe tip. In one embodiment, the tip of the probe formed from the body 510 may have a diameter ranging between about 0.1 mm and about 1.0 mm, and may have a tip radius of curvature that is less than about 20 nm. Of course, the shape of the end 515 is not limited to the shape shown in FIG. 5, and may be otherwise shaped to interface with the FIB-prepared sample 405 to remove the sample 405 from the substrate 402. For example, the end 515 may have an arcuate or substantially rectilinear concave shape, among others, including those which may aid in guiding it to the edge of the FIB-prepared sample 405.

At least a portion of the end 515 of the body 510 may be coated with a malleable layer 520. The malleable layer 520 may comprise gold, silver, indium, alloys thereof, and/or other malleable materials. As such, the end 515 may function as a compression bond end-effector configured to interface with the FIB-prepared sample 505.

During operation, the end 515 may be positioned in close proximity to or contacting the FIB-prepared sample 405 by positioning the body 510. The end 515 may subsequently be exposed to thermal, compressive and/or acoustic energy, whereby the energy may soften or melt at least a portion of the malleable layer 520 or otherwise aid in bonding the body 510 to the FIB-prepared sample 405. The FIB-prepared sample 405 may include a layer of material having substantial hardness, such as platinum or tungsten, to provide a hard surface against which the body 510 may be pressed.

Figure 6:
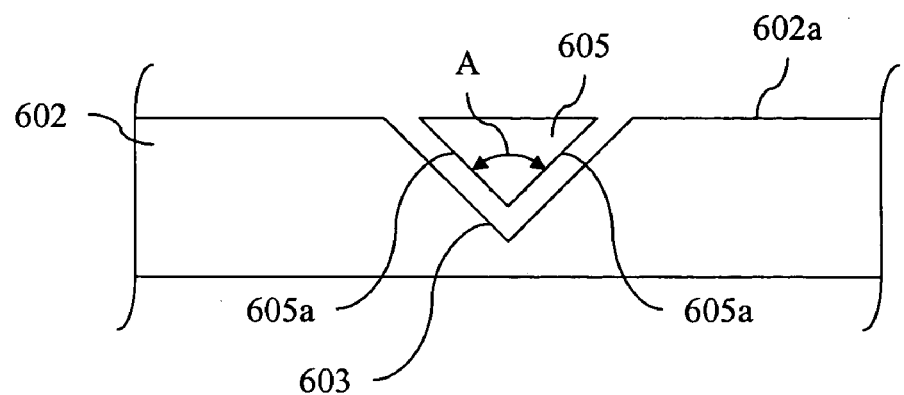
FIG. 6 is a sectional view of at least a portion of one embodiment of a substrate having an FIB-prepared sample according to aspects of the present disclosure.

Referring to FIG. 6, illustrated is a sectional view of another embodiment of the FIB-prepared sample 405 according to aspects of the present disclosure, herein designated by the reference numeral 605. The sample 605 may be substantially similar in composition and manufacture to the sample 405 described above. The sample 605 may be prepared by two (or more) FIB passes. For example, for the embodiment shown in FIG. 6, the sample 605 may be formed by making at least two FIB passes that are oriented at an acute angle relative to a surface 602a of the substrate 602. The substrate 602 may be substantially similar to the substrates described above. The acute angle may be about 45 degrees, as in the illustrated embodiment, although other angles are also within the scope of the present disclosure. Thus, the relative angle A between the sidewalls 605a of the sample 605 may be about 90 degrees, as in FIG. 6, but may also range between about 10 degrees and about 150 degrees, although other embodiments are also within the scope of the present disclosure.

In some embodiments, the triangular or wedge-shaped cross-section of the sample 605 may aid in the secure capture of the sample 605 by a grasping element, such as the grasping elements described above. Of course, the cross-sectional shape of the sample 605 may be otherwise shaped while still aiding such capture, including other cross-sectional shapes having one or more tapered sidewalls 605a or otherwise having a varying width, including embodiments in which the width does not vary linear (e.g., a stepped profile). In one embodiment, the outer-profile of the sample 605 may substantially or at least partially conform or otherwise cooperate with an inner profile of a recess or opening in the grasping element employed to capture the sample 605, such as the grasping elements 400A, 400B, and/or 400C described above.

Figure 7:
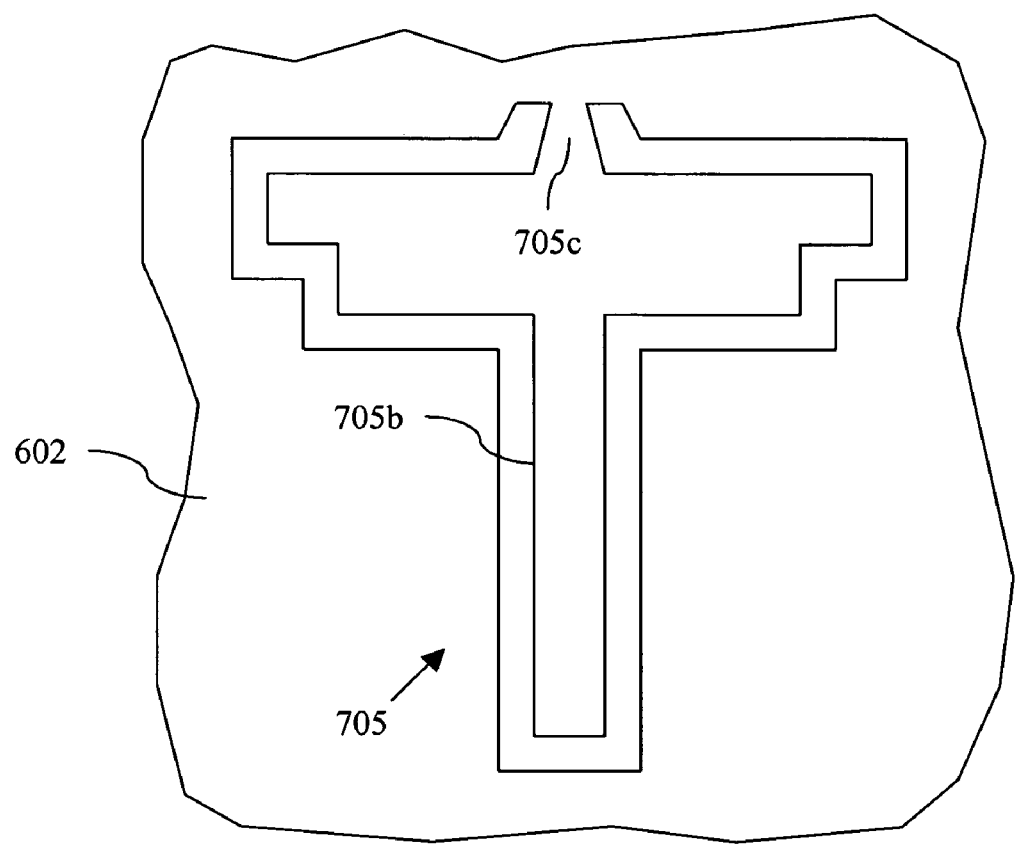
FIG. 7 is a top view of at least a portion of one embodiment of a substrate having an FIB-prepared sample according to aspects of the present disclosure.

Referring to FIG. 7, illustrated is a top view of another embodiment of the samples 405 described above according to aspects of the present disclosure, herein designated by the reference numeral 705. The sample 705 may be substantially similar in composition and manufacture to the samples 405, 605. The sample 705 includes a non-rectangular perimeter 705b. Of course, samples having a perimeter shape other than the perimeter 705b shown in FIG. 7 are also within the scope of the present disclosure.

The sample 705 may also include a thin, possibly tapered portion 705c connecting the sample 705 to the substrate 602. In other embodiments, a similarly positioned notched portion or otherwise configured portion may be employed in addition to, or in the alternative to, the tapered portion 705c. Such a tapered, necked, thinned, notched, or otherwise shaped region may provide a weakened portion of the sample 705 at which stress may concentrate in response to urging the sample 705 away from the substrate 602, such as may be performed after grasping the sample 705 with a grasping element, including the grasping elements described above. Of course, in the alternative to employing such a portion 705c, or in addition thereto, a portion of the substrate 602 connecting the substrate 602 and the sample 705 may be severed, such as by employing a laser, micromachining, selective etching, and/or other processes.

Various aspects of grasping element manufacturing, sample preparation, sample transfer and orientation, and sample examination within the scope of the present disclosure may be automated. For example, one or more manipulators (each of which may be or include an embodiment of the handling assembly 150 shown in FIG. 1) may be employed to place and/or orient a sample in an FIB chamber, possibly on a sample stage. Thus, automated sample exchange may be employed during one or more processes according to aspects of the present disclosure. The one or more manipulators may be employed to place samples onto a grid holder, which may be fixedly mounted and/or mounted on an additional positioning mechanism.

A control apparatus, which may be or include a personal computer or other computing device (hereafter collectively referred to as a "PC"), may locate and orient the sample under question. Such location and/or orientation may employ an imaging beam of a microscope, such as a scanning electron microscope (SEM), a transmission electron microscope (TEM), other electron microscopes, an optical microscope, or other type of microscope. Such location and/or orientation may also or alternatively employ other means that may be configured to orient a manipulator, handling assembly, grasping element, end effector, or component thereof, including robotic components, relative to the imaging apparatus.

Note that although the provisions of the present application may refer specifically to employment of or use with an SEM or TEM, such as during an examination process or stage thereof, aspects of the present disclosure are applicable or readily adaptable to applications employing microscopes other than a TEM. For example, in one embodiment, sample preparation may be performed in an FIB apparatus chamber, the prepared sample may be grasped and separated from its substrate while still in the FIB chamber, and the separated sample may be examined in a TEM apparatus chamber. However, in other embodiments, the sample may be prepared in a chamber of a dual-purpose FIB/SEM tool or other chamber other than a dedicated FIB chamber, and the sample may collectively be grasped and separated from its substrate and subsequently examined in a TEM chamber. In some embodiments, one or more or each of the sample preparation, capture, severing, examination, and other manipulation may be performed or assisted by automation, including via robotics or other automated apparatus contained within an FIB chamber, an SEM chamber, a TEM chamber, or other microscopy apparatus chambers.

The PC may locate the relative position of a grasping element (such as the grasping elements described above with reference to the figures herein), such as relative to the sample under question, possibly employing the imaging beam of the electron microscope. In one embodiment, an optical microscope may also or alternatively be employed, wherein the PC and/or another device may include feature detection software employed during such determination of relative positions. The PC may then drive the grasping element to a position above or otherwise proximate the sample, lower the grasping element to engage the sample with the grasping element, and then close the grasping element to secure the sample. As discussed above, the process of closing the grasping element to secure the sample may include activation or deactivation of the grasping element, or merely translating the grasping element relative to the sample may allowed the grasping element to close or otherwise secure the sample.

In some embodiments, an additional FIB cut and/or other process may be required to separate the sample from the substrate. Thereafter, or alternatively, the sample is pulled away from the substrate by the manipulator. The manipulator may then locate a grid placement position, possibly employing sensors and/or vision feedback, such as from the imaging beam. The sample may then be aligned with the grid placement position. In some embodiments, a gas may be injected at the surface of the grid placement position, such as to clean, decontaminate, or otherwise condition the surface.

The manipulator may then align and engage the sample to the grid, and the FIB beam may be employed to weld or otherwise affix the sample on the grid. In other embodiments, other means may be employed to fix the position and/or orientation of the sample, such as by securing (or leaving secured) and orienting the sample with a grasping element, such as those described above. However, if the sample is affixed to the grid, the sample may also then be disengaged from the grasping element, and the manipulator may pull away.

Additional aspects of such lift out ("pick") process and placing processes are described below. Note that although many of the aspects described below are described with regard to pick processes, such aspects are applicable or readily adaptable to placing processes.

To enable the automation of the above-described processes, the various devices providing operability of the grasping elements, grasping members, handling assembly, and manipulator, the examination of the sample, and/or any process control measuring capabilities may be communicatively coupled as an Automated Microscopy Sample Preparation System (wherein Microscopy may refer to one or more of SEM, STM, TEM, optical, and/or other microscopy apparatus). Thus, communications can be sent from one device to another in order to initiate, adjust or terminate processes such as preparing a sample for introduction into a beam device, introducing a sample into a beam device, preparing samples for measurement and/or manipulation, locating a grasping element proximate a target area on the sample, activating a grasping element to make grasp, engage, or otherwise contact the target area, and manipulating a prepared sample.

In addition, to enable the automation of such processes, the Automated Microscopy Sample Preparation System may comprise a Reference System so that the moving components of the various devices comprising the Automated Microscopy Sample Preparation System can be referenced to each other, and to fixed devices comprising the system (e.g., moving-part-to-moving-part and moving-part-to-fixed-part). By referencing the moving components of the various devices to each other, a grasping element can be automatically positioned relative to features of a sample that one wishes to process. Moreover, as the various devices of the Automated Microscopy Sample Preparation System are communicatively coupled, information gathered by the Reference System can be communicated among the devices to initiate, monitor, adjust, terminate, or collect data related to a particular process performed by a device.

The Reference System may comprise devices such as location sensors, pressure sensors, environmental sensors, material/element sensors, timers, and/or location procedures (such as locating by imaging), operable to gather information regarding the various devices employed in or with the Automated Microscopy Sample Preparation System and to gather information regarding the processes performed by the devices employed in or with the Automated Microscopy Sample Preparation System. The Reference System may also comprise programming/software for converting the information gathered by the sensors, timers and/or location procedures into messages that can be communicated among the devices. For example, the messages from the Reference System may be in the form of an electronic signal, or may be in the form of a command generated by software associated with the Reference System.

In one embodiment, the Reference System is implemented as a part of a Control Routine that is programmed into one of the communicatively coupled devices of the Automated Microscopy Sample Preparation System. In one such example, the Reference System is implemented in the Control Routine as a set of procedures that are programmed into a position control device that provides operability to the grasping element. The Control Routine may also comprise various sub-routines for enabling the automated sample preparation disclosed herein, among other sub-routines.

Particulars of such a Reference System may vary depending on the type of automated process to be performed. For example, the information required by the Reference System to effect preparation of a sample as an automated process will vary from the information required by the Reference System to effect the taking of a measurement of a sample as an automated process. In general, however, regardless of the type of automated process being performed, the Reference System may generally rely on certain factors, such as the position of the sample relative to the beam produced by the charged particle beam device, the position of the grasping element relative to the sample, and/or a "map" of the sample. A "map" of the sample refers to data regarding the sample that can be used to determine the location of features on the sample. For example, the sample may be a semiconductor chip with certain features formed thereon. A map of the sample chip provides location information regarding one or more features of samples that need to be processed. A map of a sample can be obtained from a variety of sources including but not limited to CAD data, manual training of the sample by the user, and a set of reference coordinates specified by a user or external system. Alternatively, the samples that need to be processed could be automatically detected and processed, hence the map is dynamically created and discovered by the automation itself.

The Reference System may employ information obtained from a process implemented by the Control Routine for determining the position of a sample positioned in a sample chamber of a charged particle beam device relative to the beam of the charged particle beam device. Alternatively, or additionally, the Control Routine may include a process for determining where the sample is relative to a positioning stage or grasping element, and then discovering where the stage or grasping element is, relative to the beam. Alternatively, or additionally, the Control Routine may include a process for determining the grasping element position relative to a positioning stage, and then discovering the stage position relative to the beam. According to one example, the Control Routine implements a standard image analysis procedure to determine the position of a sample relative to the beam or a positioning stage or a grasping element. For example, the image can be derived from a representation created from the scanned charged particle beam or other such device that can create a suitable representation for use by image analysis software. Reference features on the sample and/or stage and/or grasping element can be employed in the image analysis to create a mathematical coordinate system to describe to the Reference System the position/orientation of the sample and/or stage and/or grasping element.

The Reference System may also employ information obtained from a process implemented by the Control Routine for determining the position/orientation of the grasping element relative to the position of the sample in the sample chamber. There are several possible ways to effect this process. According to one example, the position/orientation of the grasping element relative to the beam or stage is determined using suitable image analysis techniques. Alternatively, or additionally, the position/orientation of the grasping element relative to the handling assembly is determined, and then the position/orientation of the grasping element relative to the beam or stage is determined. The position/orientation of the grasping element can be determined by using a technique such as image analysis, or by moving to a mechanical or electrical or laser sensor that provides suitable feedback for such a requirement.

Possibly employing a map obtained as described above, the Reference System may communicate information to a device providing operability of the grasping element, such as a positioner control device, which triggers the device to drive the position of the grasping element over the specified features or to an otherwise desired position/orientation. For example, the coordinates of the features relative to the map and the actual location of the sample under inspection, as it is positioned in the sample chamber, and/or the actual location of the grasping element and/or the actual location of the positioners can be mathematically combined.

Figure 8:
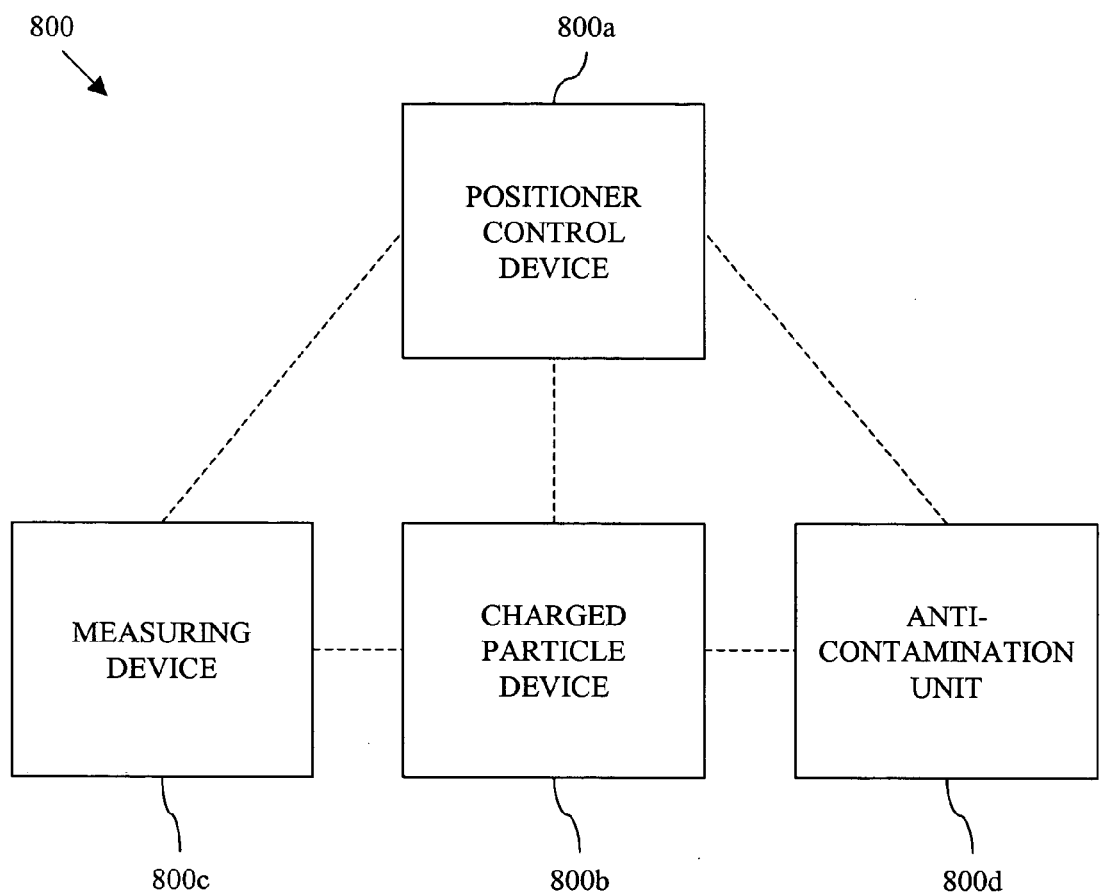
FIG. 8 is a block diagram of at least a portion of one embodiment of a system according to aspects of the present disclosure.

Referring to FIG. 8, illustrated is a block diagram of at least a portion of one embodiment of an Automated Microscopy Sample Preparation System in which the above-described Reference System may operate. According to the exemplary Automated Microscopy Sample Preparation System illustrated in FIG. 8, the system 800 comprises a positioner control device 800*a* including and/or operable to control, for example, a handling assembly (such as assembly 150 shown in FIG. 1) to which grasping elements are coupled, a charged particle beam device 800*b*, and a measuring device 800*c*. Aspects of the positioner 800*a* and the handling assembly 150 described above may be similar, such that in some instances in the following description it may be appropriate to use these terms interchangeably.

By way of example, a positioner control device 800*a*, such as the S100 Nanomanipulator System commercially available from Zyvex Corporation, may be coupled into the Automated Microscopy Sample Preparation System as disclosed herein. Also by way of example, a measuring device 800*c*, such as the Keithley 4200, which is also commercially available, may be coupled into the Automated Microscopy Sample Preparation System as disclosed herein. Similarly, a charged particle beam device 800*b*, such as an SEM or FIB available from FEI, LEO, Hitachi or JEOL, may be coupled into the Automated Microscopy Sample Preparation System. An anti-contamination unit 800*d*, such as the Evactron Model 30, which is also commercially available, may also be coupled into the Automated Microscopy Sample Preparation System as disclosed herein.

The positioner control device 800*a*, charged particle beam device 800*b*, measuring device 800*c*, and/or anti-contamination unit 800*d* may be coupled such that communications are sent from one device to another in order to initiate and/or control processes such as introducing a sample into a charged particle beam device, preparing a grasping for processing the sample, locating the grasping element proximate a target area on the sample, activating the grasping element to make contact with the target area, and/or processing the sample. The communications among the devices may be interpreted by the Control Routine, which may be programmed into one of the devices in the system 800. The Control Routine may operate to instruct the devices making up the system 800 to initiate, monitor, collect data related to, adjust or terminate a particular process, such as preparing a sample or grasping element, in response to communications received from the charged particle beam device 800*b* or other device coupled with the system 800.

According to one example, the Control Routine is programmed into a single computer or machine (e.g., a "master control computer") that is responsible for directing operation of one or more of the positioner control device 800*a*, charged particle beam device 800*b*, measuring device 800*c*, and/or anti-contamination unit 800*d*, and is also responsible for controlling a plurality of the foregoing procedures. For example, a procedure for introducing a sample into a charged particle beam device may be controlled by the same computer that operates a position control device and drives the grasping element to a desired location. In addition, Data Acquisition boards can be implemented on the computer or machine operating the position control device, for example, to enable the device to take measurements or perform processes that would otherwise be implemented by a computer, machine or operation system of the measuring device.

In an example where the Control Routine and operation of one or all of the devices of the Automated Microscopy Sample Preparation System reside on a single machine, the communication among the various devices is enabled via software. According to another example, one or more of the positioner control device 800*a*, charged particle beam device 800*b*, measuring device 800*c*, and anti-contamination unit 800*d* comprises a separate computer or machine to direct its operation. In such an example, each device is communicatively coupled by pathways such as wire, cable, network (i.e. TCP/IP network over Ethernet, 1394 connection), or wireless protocol, among others. Thus, communications between the devices of the Automated Microscopy Sample Preparation System can described as logical operations/subsystems that are accessed via a separate computer via a physical network, or may reside locally to the master control computer.

Figure 9:
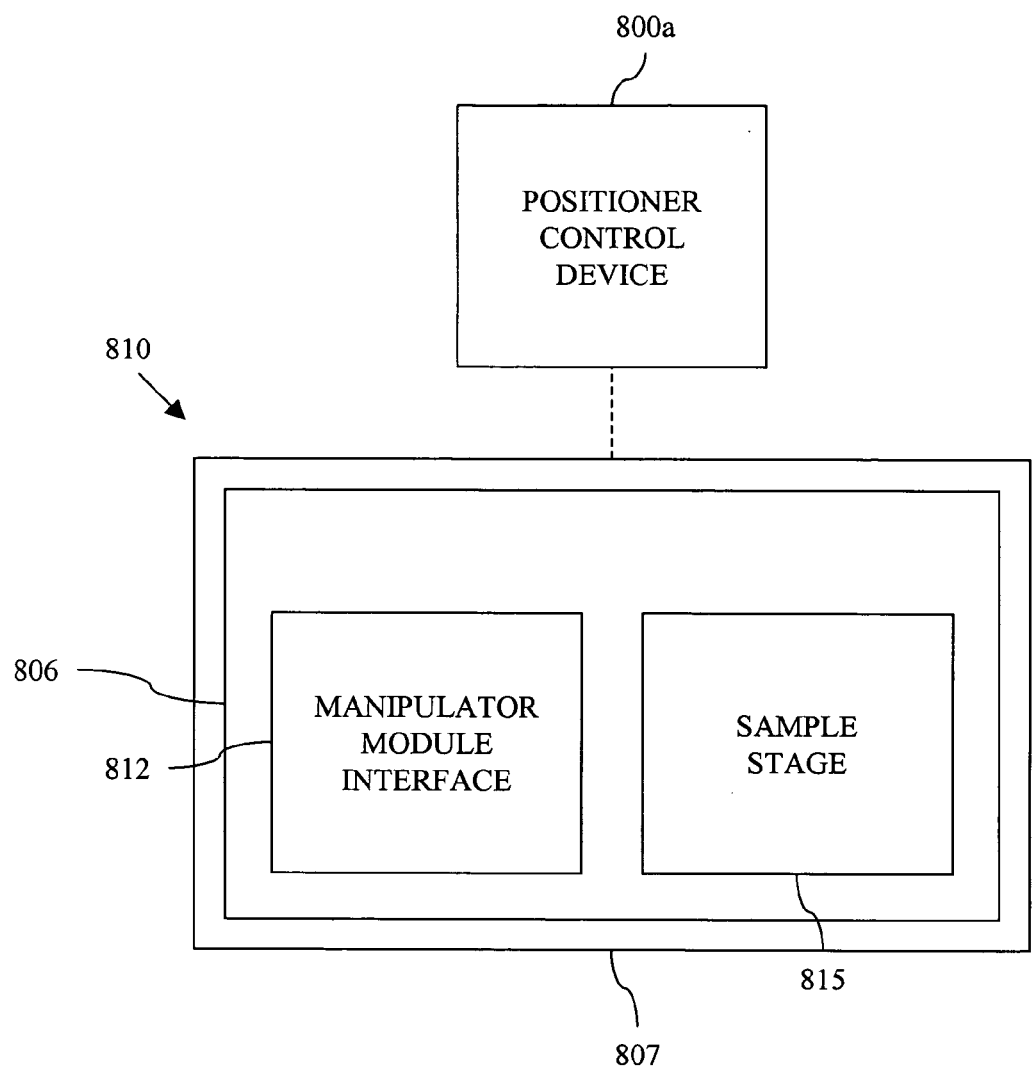
FIG. 9 is a block diagram of one embodiment of a portion of the system shown in FIG. 8 according to aspects of the present disclosure.

Referring to FIG. 9, at least a portion of an exemplary configuration for enabling the devices comprising the system 800 to communicate is illustrated as a block diagram. In this example configuration, a manipulation platform 810 for manipulating a sample is illustrated. Manipulation as used herein includes but is not limited to moving a sample in X, Y, and Z directions, and possibly determining physical and chemical characteristics of a sample, such as performing electrical, mechanical, optical, or chemical measurements, or combinations thereof. The manipulation platform 810 may include a base 806 on which a manipulator module interface site is arranged, such as site 812, although in some embodiments more than one manipulator module interface site may be included on the base 806. The manipulator module interface site 812 may be capable of receiving a manipulator or similarly configured module, such as described in U.S. patent application Ser. No. 10/173,543, the entire disclosure of which is hereby incorporated by reference herein.

The platform 810 may comprises a sample stage 815 for receiving a sample to be manipulated. The platform 810 may also include an interface 807 that enables base 806 to be coupled to a charged particle beam device 800*b*, such as an SEM/FIB. In an example where the charged particle beam device 800*b* is an SEM/FIB, a sample is arranged on sample stage 815 and the manipulation platform 810 is disposed within the sample chamber of the SEM/FIB by way of a coupling to the SEM FIB via interface 807. Thus, for example, once platform 810 is coupled to an SEM/FIB, a sample arranged on sample stage 815 can be imaged at the same time as the manipulator module(s) which are utilized to manipulate the sample.

As further shown in FIG. 9, a positioner control device 800*a* is coupled to manipulation platform 810. When manipulation platform 810 is coupled to a charged particle beam device 800*b* by way of interface 807, the charged particle beam device 800*b* and the positioner control device 800*a* are communicatively coupled such that communications can be sent to and from the charged particle beam device 800*b* and the positioner control device 800*a*, as well as sensors located within these devices that derive information for use in the Reference System.

The positioner control device 800*a* may be programmed for automated control over the operation of manipulator module(s) coupled to the one or more interface sites 812. According to one example, a Control Routine, possibly comprising the Reference System as a set of methods, is also programmed into the positioner control device 800*a* to instruct the devices making up the system 800 to initiate, monitor, collect data related to, adjust or terminate a particular process, such as preparing/orienting a grasping element, preparing a sample, or actuating the grasping element and/or handling assembly, in response to communications received from the charged particle beam device 800*b* or the measuring device 800*c*.

An automated sample transport system according to aspects of the present disclosure may be enabled by appropriate software and hardware to communicate information used by the Control Routine and/or the Reference System. In addition to hardware and software to enable the appropriate communications, the automated sample transport system may include a transport mechanism (for example, an electric motor, a piezoelectric motor, a MEMS motor, pneumatics for mechanical actuation, or friction-reduction methods, among others) operable to transfer the sample, such as from a sample load station into the sample chamber.

According to one example, the sample is held in place by tools, clamps, bracketry, grippers, grasping elements vacuum, or otherwise, in a load station, where optional de-processing and preparation is performed. In an example where a grasping element is introduced and conditioned in situ and before the sample is introduced into the sample chamber, the grasping element may be positioned within the sample chamber and conditioned or characterized while the sample is being held in the load station. When the Control Routine receives a signal that the grasping element is properly conditioned, if such conditioning is performed, the Control Routine can then trigger a transport mechanism of the automated sample transport system to introduce the sample into the sample chamber.

In situ processing of the sample may include performing one or more FIB cuts, such as to define the profile and/or cross-section of the sample, among other processes. In situ processing may also or alternatively include decontamination of the sample and/or substrate surface, such as by employing an EVACTRON® SEM-CLEAN™ device commercially available from XEI Scientific, Redwood City, Calif. Generally, an EVACTRON® SEM-CLEAN™ device uses a low-powered RF plasma to make oxygen radicals from air that then oxidize and chemically etch away hydrocarbons from the interior of an SEM or other microscope. Other additional or alternative processing may include FIB sputtering, ion gun sputtering, and plasma or radical cleaning, any of which can be implemented through sub-routines of the Control Routine.

Subsequent to introduction, and after optional in-situ preparation and conditioning of the sample, if performed, the presence of the sample is communicated to the Control Routine. Regardless of whether the sample is positioned within the sample chamber before or after the grasping element, and possibly upon receiving information that the grasping element has been properly conditioned and/or that the sample is grounded in the sample chamber, the Control Routine will access the Reference System and the positioner control device to locate the grasping element above or otherwise proximate the sample or a feature of interest thereon. For example, features of interest on the sample may be TEM Sample coupon points at which the grasping element may ultimately acquire the sample or otherwise make contact, and may thus referred to as "acquisition contact points". "Above" the acquisition contact points may describe a position from which a "final" trajectory to the acquisition contact point can be determined and executed. According to one example, such a position is normal to the plane in which the contact acquisition points reside. Location of the grasping element proximate the acquisition contact points may be implemented by or employing the Reference System.

As described above, the Reference System enables the moving (and stationary) components of the various devices comprising the Automated Microscopy Sample Preparation System to be referenced to each other as well as to the microscope. Thus, information regarding the relative positions of the sample, the grasping element, the handling assembly, and/or a map of the sample is used by the Reference System to provide the appropriate messages to the Control Routine, which communicates the appropriate messages to the positioner control device to move the grasping element such that the grasping element is appropriately positioned, such as relative to the contact acquisition points. Other approach methods where the grasping element is not in contact with the desired acquisition contact points and are not necessarily directly above the acquisition contact points, but may still be moved into contact with the acquisition contact point, can also be implemented according to aspects of the present disclosure.

Once the Control Routine has messaged the positioner control device with the appropriate locations, the positioner control device contains the appropriate hardware and software to move a positioner, handling assembly or other device controlling the grasping element to those locations. As one example, the positioner control device 800a operates a positioner and a manipulation module in a manner as described in U.S. patent application Ser. No. 10/173,543.

The Control Routine augments the operation of the positioner control device 800a with one or more sub-routines for grasping-element-positioning, wherein the sub-routines may monitor and/or detect the positioning of the grasping element relative to the contact acquisition points registered by the Reference System. The grasping element positioning sub-routines also implement procedures for determining when a grasping element has reached the desired location above an acquisition contact point. Exemplary procedures for grasping element positioning and determining when the grasping element has reached the desired location include but are not limited to image processing effected by the charged particle beam device, location of alignment marks with the charged particle beam, reference to map data obtained by the Reference System, operation of the charged particle beam device in a teaching mode, reference to absolute coordinates on the sample (such as a list of coordinates previously determined), and an automated or semi-automated "point and click" process.

Of course, aspects of one or more steps or processes employed in the above-described sample preparation, lift-out, relocation, orientation, and/or positioning may be automated in addition to (or in the alternative to) the automation aspects described in the immediately preceding paragraphs. For example, many automation aspects are described in U.S. Provisional Application No. 60/546,840. Although many automation aspects are described therein in the context of probing or preparing a sample or wafer, such aspects are applicable or readily adaptable to additional processes for sample preparation, lift-out, manipulation, examination, and other processes described herein, and are fully within the scope of the present disclosure.

Thus, the present disclosure provides a method including, in one embodiment, severing a sample at least partially from a substrate by cutting the substrate with a focused ion beam (FIB), capturing the substrate sample by activating a grasping element, and separating the captured sample from the substrate.

Another embodiment of a method according to aspects of the present disclosure includes: (1) severing a sample at least partially from a substrate by cutting the substrate with a focused ion beam (FIB); (2) positioning an assembly tool proximate the sample, the assembly tool having a compression bond end-effector configured to capture the sample; (3) applying a force on the sample through the compression bond end-effector, the force having sufficient magnitude to cause a compression bond to form between the compression bond end-effector and the sample, thereby capturing the sample; and (4) separating the captured sample from the substrate.

The present disclosure also introduces a system including, in one embodiment, focused ion beam (FIB) means for at least partially severing a sample from a substrate, a grasping element configured to capture the sample, means for activating the grasping element to capture the sample, and means for separating the captured sample from the substrate.

A grasping element for capturing an FIB-prepared sample is also provided in the present disclosure. In one embodiment, the grasping element includes a body configured to be coupled to a handling assembly, an actuating member coupled to the body, and a grasping member coupled to the actuating member and configured to capture an FIB-prepared sample in response to activation of the actuating member.

Another embodiment of a method according to aspects of the present disclosure includes: (1) severing a sample at least partially from a substrate by cutting the substrate with a focused ion beam (FIB); (2) capturing the substrate sample with a grasping element; (3) separating the captured sample from the substrate; and (4) releasing the captured substrate sample by activating the grasping element. One or more of the sample severing, the sample capture, the sample separation, and the sample release may be automated.

The foregoing has outlined features of several embodiments so that those skilled in the art may better understand the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A system, comprising:
    focused ion beam (FIB) means for at least partially severing a sample from a substrate;
    a grasping element configured to mechanically capture the sample;
    means for mechanically activating the grasping element to mechanically capture the sample; and
    means for separating the captured sample from the substrate.

2. The system of claim 1 further comprising means for transporting the captured sample to a microscope for examination.

3. The system of claim 2 wherein the microscope is a transmission electron microscope.

4. The system of claim 2 wherein the microscope is a scanning electron microscope.

5. The system of claim 2 wherein the microscope is a scanning transmission electron microscope.

6. The system of claim 1 wherein the grasping element includes an integral actuator for mechanically configuring the grasping element between opened and closed positions.

7. The system of claim 1 wherein the grasping element includes a thermally-activated end-effector configured to mechanically capture the sample upon at least one of heating and cooling of the end effector.

8. The system of claim 7 wherein the grasping element includes an integral heater configured to activate the end effector.

9. The system of claim 8 wherein the integral heater is resistively heated.

10. The system of claim 1 wherein the grasping element comprises a malleable end-effector and the means for activating the grasping element includes means for pressing the end-effector against the sample to form a compression bond.

11. The system of claim 1 wherein the grasping element is configured to secure the sample during examination.

12. The system of claim 1 wherein the means for activating the grasping element includes automated means for activating the grasping element to capture the sample via automation.

13. The system of claim 1 wherein the means for separating the captured sample from the substrate includes automated means for separating the captured sample from the substrate via automation.

14. The system of claim 1 further comprising automation means for controlling:
    the FIB means during the at least partial severing;
    the activating means during the sample capture; and
    the separating means during the sample separation.

15. A grasping element for capturing an FIB-prepared sample, comprising:
    a body configured to be coupled to a handling assembly;
    an actuating member coupled to the body; and
    a grasping member coupled to the actuating member and configured to mechanically capture an FIB-prepared sample in response to mechanical actuation of the actuating member.

16. The grasping element of claim 15 wherein the mechanical actuation is electro-thermal actuation.

17. The grasping element of claim 15 wherein the grasping member is a first one of a plurality of grasping members.

18. The grasping element of claim 17 wherein ones of the plurality of grasping members are substantially mirror images of one another.

19. The grasping element of claim 15 wherein the grasping member includes a first profile corresponding to a second profile of the FIB-prepared sample.

20. The grasping element of claim 19 wherein the first profile is substantially non-rectangular.

21. A grasping element for capturing an FIB-prepared sample, comprising:
    a body configured to be coupled to a handling assembly;
    an actuating member coupled to the body; and
    a grasping member coupled to the actuating member, the grasping member configured to mechanically capture an FIB-prepared sample, the grasping member further configured to release the FIB-prepared sample in response to mechanical actuation of the actuating member.

22. The grasping element of claim 21 wherein the grasping member is configured to passively capture the FIB-prepared sample.

23. The grasping element of claim 21 wherein the mechanical actuation is electro-thermal actuation.

24. The grasping element of claim 21 wherein the grasping member is a first one of a plurality of grasping members.

25. The grasping element of claim 24 wherein ones of the plurality of grasping members are substantially mirror images of one another.

26. The grasping element of claim 21 wherein the grasping member includes a first profile corresponding to a second profile of the FIB-prepared sample.

27. The grasping element of claim 26 wherein the first profile is substantially non-rectangular.

28. An apparatus, comprising:
means for cutting a substrate with a focused ion beam (FIB) to at least partially sever a sample from the substrate;
means for mechanically activating a grasping element to capture the substrate sample with the grasping element; and
means for separating the captured sample from the substrate.

29. The apparatus of claim 28 wherein at least a portion of at least one of the cutting means, activating means, and separating means is automated.

30. The apparatus of claim 28 further comprising means positioning the grasping element proximate the substrate sample, wherein the positioning means is at least partially automated.

31. The apparatus of claim 28 further comprising means for transporting the captured sample to an electron microscope, wherein the transporting means is at least partially automated.

32. The apparatus of claim 28 wherein the activating means is configured to activate the grasping element to capture the substrate sample after the substrate sample has been only partially severed from the substrate, and the cutting means is configured to completely sever the partially severed substrate sample from the substrate while the partially severed sample is captured by the grasping element.

33. The apparatus of claim 32 wherein the cutting means is configured to completely sever the partially severed substrate sample by cutting a connection between the partially severed substrate sample and the substrate.

34. The apparatus of claim 33 wherein the cutting means is configured to cut the connection via FIB.

35. The apparatus of claim 28 wherein the separating means is configured to reposition the captured sample relative to the substrate until a connection between the sample and the substrate is compromised.

36. The apparatus of claim 28 wherein the activating means includes means for adjusting an amount of electrical power delivered to the grasping element to mechanically capture the substrate sample with the grasping element.

37. The apparatus of claim 28 wherein the activating means includes means for switching between an electrically powered state and an electrically un-powered state to mechanically capture the substrate sample with the grasping element.

38. The apparatus of claim 28 wherein the activating means includes means for increasing an amount of electrical power delivered to the grasping element to mechanically capture the substrate sample with the grasping element.

39. The apparatus of claim 28 wherein the activating means includes means for substantially ceasing delivery of electrical power to the grasping element to mechanically capture the substrate sample with the grasping element.

40. The apparatus of claim 28 wherein the activating means includes means for actuating the grasping element to mechanically open and close the grasping element.

41. The apparatus of claim 40 wherein the actuating means includes electro-thermal actuating means operable to mechanically open and close the grasping element.

42. The apparatus of claim 40 wherein the actuating means includes electrostatic actuating means operable to mechanically open and close the grasping element.

43. The apparatus of claim 40 wherein the actuating means includes piezoelectric actuating means operable to mechanically open and close the grasping element.

44. The apparatus of claim 28 further comprising the grasping element, wherein the grasping element includes a thermally activated end-effector, and wherein the activating means includes at least one of:
means for heating at least a portion of the grasping element, the heating means operable to mechanically open and close the grasping element; and
means for cooling at least a portion of the grasping element, the cooling means operable to mechanically open and close the grasping element.

45. The apparatus of claim 28 further comprising means for examining the sample while the sample remains captured by the grasping element.

46. The apparatus of claim 28 further comprising means for examining the sample after the sample is released from the grasping element.

47. The apparatus of claim 46 further comprising means for manipulating the grasping element to position the sample on an examination grid prior to the examination of the sample.

48. The apparatus of claim 46 further comprising means for coupling the sample to an examination grid prior to the releasing the sample from the grasping element.

49. The apparatus of claim 28 wherein the grasping element is a mechanically-actuated MEMS element.

50. The apparatus of claim 49 wherein the MEMS element comprises nickel.

51. The apparatus of claim 49 wherein the MEMS element comprises silicon.

52. The apparatus of claim 28 wherein the activating means includes means for pressing the grasping element against the substrate sample.

53. The apparatus of claim 52 wherein the grasping element includes a malleable layer configured to interface with the substrate sample.

54. The apparatus of claim 53 wherein the malleable layer comprises gold.

55. The apparatus of claim 28 wherein:
the cutting means includes means for cutting each of a plurality of samples at least partially from a substrate; and
the separating means includes means for separating each of the plurality of samples from the substrate.

56. The apparatus of claim 28 wherein the cutting means, the activating means, and the separating means are each configured for installation into a transmission electron microscope (TEM) and operation within the TEM.

57. The apparatus of claim 28 wherein the cutting means, the activating means, and the separating means are each configured for installation into a scanning electron microscope (TEM) and operation within the SEM.

58. An apparatus, comprising:
means for cutting a substrate with a focused ion beam (FIB) to at least partially sever a sample from the substrate;
means for positioning an assembly tool proximate the sample, the assembly tool having a compression bond end-effector configured to capture the sample;
means for applying a force on the sample through the compression bond end-effector, the force having sufficient magnitude to cause a compression bond to form between the compression bond end-effector and the sample, thereby capturing the sample; and
means for separating the captured sample from the substrate.

59. The apparatus of claim 58 further comprising means for transporting the captured sample to an electron microscope.

60. The apparatus of claim 58 wherein the force applying means includes means for actuating an actuator to which the compression bond end-effector is coupled.

61. The apparatus of claim 60 wherein actuating includes electro-thermally activating.

62. The apparatus of claim 60 wherein actuating includes electro-statically activating.

63. An apparatus, comprising:
    means for cutting a substrate with a focused ion beam (FIB) to at least partially sever a sample from the substrate;
    means for capturing the substrate sample with a grasping element without activating the grasping element; and
    means for activating the grasping element to release the captured substrate sample from the grasping element.

64. The apparatus of claim 63 wherein the capturing means includes means for passively capturing the substrate sample with the grasping element.

65. The apparatus of claim 63 wherein the grasping element is configured to maintain a substantially constant temperature while the substrate sample is being captured with the grasping element.

66. The apparatus of claim 63 wherein the grasping element is configured to passively capture the substrate sample.

67. The apparatus of claim 63 wherein the grasping element is configured to passively capture the substrate sample in the substantial absence of electrical power delivered to the grasping element.

68. The apparatus of claim 63 wherein the capturing means includes means for capturing the substrate sample while the grasping element is in a non-activated state.

69. The apparatus of claim 63 wherein the capturing means includes means for capturing the substrate sample while substantially no electrical power is delivered to the grasping element.

* * * * *